United States Patent
Aotsuka et al.

(10) Patent No.: US 6,642,250 B2
(45) Date of Patent: Nov. 4, 2003

(54) 1,8-NAPHTHYRIDIN-2(1H)-ONE DERIVATIVES

(75) Inventors: Tomoji Aotsuka, Tokyo (JP); Kentarou Kumazawa, Tokyo (JP); Nagatoshi Wagatsuma, Tokyo (JP); Kouki Ishitani, Tokyo (JP)

(73) Assignee: Grelan Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/889,107
(22) PCT Filed: Dec. 7, 2000
(86) PCT No.: PCT/JP00/08671
§ 371 (c)(1),
(2), (4) Date: Jul. 11, 2001
(87) PCT Pub. No.: WO01/42244
PCT Pub. Date: Jun. 14, 2001

(65) Prior Publication Data
US 2003/0036651 A1 Feb. 20, 2003

(30) Foreign Application Priority Data
Dec. 8, 1999 (JP) ............................................. 11-349130

(51) Int. Cl.⁷ ...................... A61K 31/44; C07D 513/02
(52) U.S. Cl. ........................................ 514/300; 546/113
(58) Field of Search ................................. 546/123, 113; 514/300

(56) References Cited

U.S. PATENT DOCUMENTS 4,945,095 A * 7/1990 Smith et al.
5,189,045 A * 2/1993 Peglion et al.

FOREIGN PATENT DOCUMENTS

| EP | 428437 | * 5/1991 |
|----|--------|----------|
| IE | 55113 | 6/1990 |
| JP | 58-194887 | 11/1983 |
| JP | 7-10875 | 1/1995 |
| JP | 11/106385 | 4/1999 |
| WO | 99/7704 | 2/1999 |

* cited by examiner

Primary Examiner—Alan L. Rotman
Assistant Examiner—Binta Robinson
(74) Attorney, Agent, or Firm—Wenderoth, Lind & Ponack, L.L.P.

(57) ABSTRACT

The purpose is to provide selective PDE IV inhibitors which have a potent anti-asthmatic profile with excellent safety. A compound of the formula (1):

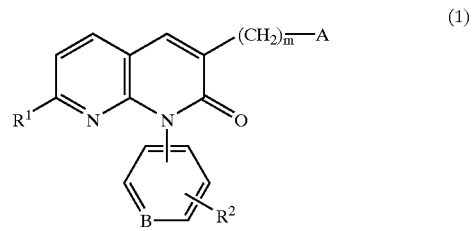

wherein:
A is an unsubstituted or optionally substituted 5 or 6 membered heteroaryl group or a fused benzene ring in which any of the above-defined heteroaryl groups is fused to a benzene ring,
B is carbon or nitrogen,
$R^1$ is hydrogen, lower alkyl, trifluoromethyl, hydroxyl, lower alkoxy, a residue derived from a carboxylic acid or a derivative thereof, amino, or an amino nitrogen-containing group,
$R^2$ is hydrogen, halogen, cyano, nitro, lower alkylthio, lower alkylsulfinyl, lower alkylsulfonyl, trifluoromethyl, hydroxyl, lower alkoxy, a residue derived from a carboxylic acid or a derivative thereof, amino, or an amino nitrogen-containing group, and
m is an integer of from 1 to 8, both inclusive;
or a pharmaceutically acceptable salt thereof possesses selective PDE IV inhibition and is useful as a pharmaceutical drug, preferably an anti-asthmatic, etc.

12 Claims, No Drawings

1,8-NAPHTHYRIDIN-2(1H)-ONE DERIVATIVES

This application is a 371 of PCT/JP00/08671 filed Dec. 7, 2000.

FIELD OF THE INVENTION

The present invention relates to novel 1,8-naphthyridin-2(1H)-one derivatives that selectively inhibit phosphodiesterase (hereinafter, referred to as "PDE") IV, or pharmaceutically acceptable salts thereof, and to pharmaceutical compositions comprising the same. The present invention also relates to prophylactic and/or therapeutic drugs (including antiasthmatics) for diseases associated with PDE IV actions, which comprise each an effective amount of at least one member selected from the 1,8-naphthyridin-2(1H)-one derivatives and salts thereof.

BACKGROUND OF THE INVENTION

PDEs are enzymes which hydrolyze intracellular cyclic AMP (cAMP) and intracellular cyclic GMP (cGMP) and widely distributed in vivo in various tissues and organs. Up to now, it has been known that PDEs are classified into 7 isoenzyme families, i.e., type I to VII PDEs (PDE I to VII), according to their properties. Among them, PDE IV is known to be an enzyme which is predominantly present in airway smooth muscle cells and a wide variety of inflammatory cells, i.e., neutrophils, eosinophils, lymphocytes, etc. and selectively breaks down cAMP. In addition, it has been known that an elevation of cAMP levels in airway smooth muscle cells leads to relaxation of the airway smooth muscles. An increase of cAMP levels in inflammatory cells has also been known to suppress an activation of inflammatory cells, including, for example, a release of cytotoxic proteins from eosinophils, etc.

Therefore, if PDE IV predominantly located in airway smooth muscle cells and inflammatory cells is inhibited by inhibitors selective for said isozyme form, an elevation of cAMP levels would be induced in such cells. As a result, it would be expected to elicit bronchodilator actions via relaxing airway smooth muscles and anti-inflammatory actions through suppressing inflammatory cell activation. Such selective inhibitors of PDE IV would be expected to become excellent anti-asthmatic agents.

Up to now, it has been known that theophylline which is a xanthine derivative, rolipram, which is a catechol derivative, etc. are inhibitors of PDE TV. Theophylline inhibits PDE in various tissues due to its non-selectivity for individual isozymes, thereby exerting not only a bronchodilator activity to be targeted but also extra actions on heart, CNS, etc. Although rolipram is observed to be selective for PDE IV, it is easily transferred into the CNS due to its property of being absorbed. Therefore, rolipram has a drawback that it induces adverse central side-actions such as an emetic action.

Under these circumstances, in order to find out pharmaceutical drugs having an excellent anti-asthmatic efficacy via minimizing undesirable side-actions in tissues and organs other than bronchial smooth muscles and inflammatory cells, inhibitors with improved selectivity for PDE IV have been screened and examined.

For instance, with an aim at such inhibitors, various compounds including diazepinoindoles (JP, A, 10-507447 (1998)), tri-substituted phenyl derivatives (JP, A, 10-504530 (1998), JP, A, 10-503174 (1998), JP, A, 10-503173 (1998), etc.), naphthalene derivatives (JP, A, 10-226647 (1998)), etc., have been proposed.

Besides these, for the purpose of developing not only anti-asthmatics but also pharmaceutical drugs for preventing and treating a wide range for diseases, PDE IV-inhibitory compounds having a naphthyridine ring have been proposed in WO 94/12499, A1; JP, A, 7-10875 (1995); WO 96/6843, A1; JP, A, 11-106385 (1999); etc.

Further, JP, A, 63-159382 (1988) discloses 1-substituted naphthyridine derivatives having, on the position 3, a substituent selected from alkyl, cycloalkyl, phenyl, phenylalkyl, etc., which are deemed useful in the treatment of allergy, inflammation, and the like, though no mention is made of PDE IV-inhibiting actions.

Such compound groups are, however, unsatisfactory in view of solving the aforementioned problems. There is still a demand for anti-asthmatics which exert more selective PDE IV-inhibiting actions and have advantageous properties from aspects regarding efficacy and safety.

For instance, over the past decade, many pharmaceutical companies have focused on the inhibition of PDE IV for the treatment of asthma. The biology of the PDE IV isozyme and the structure-activity relationship of already-reported inhibitors have recently been reviewed in the literature. In such processes, it has been pointed out that in general the therapeutic utility of selective PDE IV inhibitors, such as the prototypical agent rolipram, have been hampered by nausea and emesis limiting their therapeutic potential (J. Med. Chem., 41: 2268 to 2277 (1998)).

SUMMARY OF THE INVENTION

The present inventors have conducted an extensive research on various compounds in order to solve the above problems. As a result, the present inventors have succeeded in producing novel 1,8-naphthyridin-2(1H)-one derivatives which exert selective inhibition against PDE IV. Further, the present inventors have found that the compounds of the present invention are not only unexpectedly advantageous over the conventional PDE IV inhibitors but also qualified as potent inhibitors of PDE IV from aspects of pharmacological action and safety, and succeeded in accomplishing this invention.

The present invention, as described hereinbelow, encompasses 1,8-naphthyridin-2(1H)-one derivative compounds having a heteroaryl group, or a fused benzene ring in which any of the heteroaryl groups is fused to a benzene ring, via 1 to 8 methylene chains on the 3 position of the 1,8-naphthyridin-2(1H)-one nucleus and pharmaceutical compositions comprising an effective amount of the said compound. Since the compounds of the invention are naphthyridine derivatives having a heteroaryl group, or a fused benzene ring in which any of the heteroaryl groups is fused to a benzene ring, via 1 to 8 methylene chains on the 3 position of the 1,8-naphthyridine nucleus, it is apparent that the inventive compounds are structurally different from 1-substituted naphthyridine derivatives disclosed in JP, A, 63-159382 (1988). As described hereinbelow, the compounds of the invention are also distinct from the compounds disclosed in JP, A, 63-159382 (1988) because their PDE IV-inhibiting activity is significantly superior to that of the prior art compounds.

The present invention provides the following:
1) A compound of the formula (1):

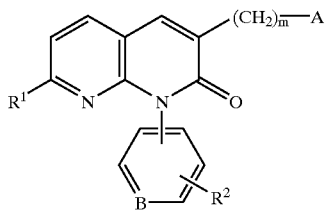

wherein:
- A is an unsubstituted or optionally substituted 5 or 6 membered heteroaryl group or a fused benzene ring in which any of the above-defined heteroaryl groups is fused to a benzene ring,
- B is carbon or nitrogen,
- $R^1$ is hydrogen, lower alkyl, trifluoromethyl, hydroxyl, lower alkoxy, a residue derived from a carboxylic acid or a derivative thereof, amino, or an amino nitrogen-containing group,
- $R^2$ is hydrogen, halogen, cyano, nitro, lower alkylthio, lower alkylsulfinyl, lower alkylsulfonyl, trifluoromethyl, hydroxyl, lower alkoxy, a residue derived from a carboxylic acid or a derivative thereof, amino, or an amino nitrogen-containing group, and
- m is an integer of from 1 to 8, both inclusive; or a pharmaceutically acceptable salt thereof.

2) The compound according to the above 1), wherein A is a 5 or 6 membered heteroaryl group and B is carbon; or a pharmaceutically acceptable salt thereof.

3) The compound according to the above 2), wherein A is pyridyl, 1-oxypyridyl, thienyl, furyl, or thiazolyl; or a pharmaceutically acceptable salt thereof.

4) The compound according to the above 2), wherein A is pyridyl or 1-oxypyridyl, and m is from 1 to 5, both inclusive; or a pharmaceutically acceptable salt thereof.

5) The compound according to the above 1), wherein A is a 5 or 6 membered heteroaryl group, and B is nitrogen; or a pharmaceutically acceptable salt thereof.

6) The compound according to the above 5), wherein A is pyridyl, 1-oxypyridyl, thienyl, furyl, or thiazolyl; or a pharmaceutically acceptable salt thereof.

7) The compound according to the above 1), wherein A is a fused benzene ring in which any of the above-defined 5 or 6 membered heteroaryl groups is fused to a benzene ring, and B is carbon; or a pharmaceutically acceptable salt thereof.

8) The compound according to the above 7), wherein A is benzothiazolyl; or a pharmaceutically acceptable salt thereof.

9) The compound according to the above 1), wherein A is a fused benzene ring in which any of the above-defined 5 or 6 membered heteroaryl groups is fused to a benzene ring, and B is nitrogen; or a pharmaceutically acceptable salt thereof.

10) The compound according to the above 9), wherein A is benzothiazolyl; or a pharmaceutically acceptable salt thereof.

11) The compound according to any of the above 1) to 10), wherein $R^1$ is hydrogen or lower alkyl; or a pharmaceutically acceptable salt thereof.

12) The compound according to any of the above 1) to 11), wherein $R^2$ is hydrogen, halogen, cyano, nitro, lower alkylthio, lower alkylsulfinyl, or lower alkylsulfonyl; or a pharmaceutically acceptable salt thereof.

13) 1-(3-Nitrophenyl)-3-(pyridin-3-ylmethyl)-1,8-naphthyridin -2(1H)-one.

14) 1-(3-Nitrophenyl)-3-[3-(pyridin-4-yl)propyl]-1,8-naphthyridin-2(1H)-one.

15) 1-(3-Methylthiophenyl)-3-[3-(pyridin-4-yl)propyl]-1,8-naphthyridin-2(1H)-one.

16) 1-(Pyridin-3-yl)-3-[3-(pyridin-4-yl)propyl]-1,8-naphthyridin-2(1H)-one.

17) A pharmaceutical composition which comprises an effective amount of a compound according to any of the above 1) to 16) or a pharmaceutically acceptable salt thereof in admixture with a pharmaceutically acceptable carrier.

18) A phosphodiesterase IV inhibitor comprising an effective amount of a compound according to any of the above 1) to 16) or a pharmaceutically acceptable salt thereof.

19) An anti-asthmatic comprising an effective amount of a compound according to any of the above 1) to 16) or a pharmaceutically acceptable salt thereof.

20) A drug for the prophylaxis and/or treatment of at least one member selected from diseases or abnormal conditions related to phosphodiesterase IV activity, said drug comprising an effective amount of a compound according to any of the above 1) to 16) or a pharmaceutically acceptable salt thereof.

21) A drug comprising an effective amount of a compound according to any of the above 1) to 16) or a pharmaceutically acceptable salt thereof, said drug for preventing and/or treating at least one disease or abnormal condition selected from the group consisting of:
(1) respiratory diseases, including bronchial asthma (including chronic bronchial asthma and atopic asthma), acute bronchitis, chronic bronchitis, asthmatic bronchitis, pneumonic diseases, pulmonary emphysema, chronic obstructive pulmonary disease (COPD), acute respiratory distress syndrome (ARDS), and the like;
(2) inflammatory diseases, including atopic dermatitis, conjunctivitis, urticaria, acquired immunodeficiency syndrome (AIDS), keloid formation, rhinitis, iridocyclitis, gingivitis, periodontitis, dentoalveolitis, gastritis, ulcerative colitis, Crohn's disease, gastrointestinal ulcer, esophagitis, myositis, encephalitis (such as myasthenia gravis, multiple sclerosis and neuritis), hepatitis, scar tissue formation, nephritis (including proliferative nephritis), peritonitis, pleurisy, scleritis, scleroderma, scalds or burns, and the like;
(3) systemic or local joint diseases, including osteoarthritis, gouty arthritis, rheumatoid arthritis, malignant rheumatism, psoriatic arthritis, and the like;
(4) inflammatory conditions associated with organ transplantation, etc., including reperfusion injury, graft versus host reaction, and the like;
(5) diseases related to urination, including diabetes insipidus, urethritis, urinary incontinence, cystitis, irritable bladder, neurogenic bladder, uremia, uriniferous tubular disorder, pollakiuria, ischuria, and the like;
(6) diseases or abnormal conditions related to tumor necrosis factor (TNF) (for example, TNF-α, etc.) and other cytokines (for example, IL-1, IL-4, IL-6, etc.), including psoriasis, rheumatoid arthritis, ulcerative colitis, Crohn's disease, septicemia, septic shock, endotoxic shock, gram negative bacillus sepsis, toxic shock syndrome, nephritis, hepatitis, infection (induced by bacteria and viruses), circulatory failure (heart failure, arteriosclerosis, myocardial infarction, cerebral apoplexy), and the like;

(7) proliferative diseases, including malignant tumors, leukemia, proliferative dermal diseases (keratosis and various types of dermatitides), connective tissue diseases and the like;

(8) diseases related to nervous function abnormality, including impaired learning, memory and recognition related to neurodegenerative disorders such as Alzheimer's disease and Parkinson's disease, multiple lateral sclerosis, senile dementia, amyotrophic lateral sclerosis, acute demyelinating neuritis, muscular dystrophy, and the like;

(9) diseases related to abnormality of mental functions, including manic-depressive psychosis, schizoid, anxiety, panic, and the like;

(10) diseases demanding protection of nerves and cells, including cardiac arrest, spinal cord injury, intermittent claudication, ischemic diseases (including angina pectoris, cardiac infarction, cerebral apoplexy, head injury, etc.) and the like;

(11) endocrine diseases, including not only diabetes but also diabetic retinopathy, diabetic nephropathy, diabetic neurosis, amyloidosis, pancreatitis, thyroiditis, obesity, prostatomegaly, and the like;

(12) autoimmune diseases, including systemic lupus erythematosus (SLE), atrophic gastritis, thyroid diseases, glomerular nephritis, orchitis, adrenal diseases, hemolytic anemia, oophoritis, and the like;

(13) cardiovascular diseases, including hypertension, angina pectoris, heart failure, myocarditis, external epicarditis, endocarditis, valvulitis, and the like;

(14) vessel and blood system diseases, including angiitis, aneurysm, endoangiosis, thromboangiitis, granulomatosis, cerebrovascular angiitis, arteriosclerosis, periangitis, leukopenia, thrombocytopenia, Boeck's sarcoid, and the like;

(15) diseases related to immune reactions or allergic responses, including contact dermatitis, serum sickness, drug allergy, Goodpasture's syndrome, lymphoma, rheumatic fever, AIDS, anaphylactic shock and the like; and

(16) other diseases, disorders or abnormal states, including glaucoma, spastic paralysis, impotence, diseases or illness accompanied with pain (contusion, headache, etc.), neck-shoulder-arm syndrome, nephropathy, renal insufficiency, hepatic insufficiency, obesity, etc.

22) The drug according to the above 20) or 21) for preventing and/or treating at least one disease or abnormal state selected from the group consisting of:

(1) respiratory diseases selected from the group consisting of bronchial asthma including chronic bronchial asthma and atopic asthma; acute bronchitis; chronic bronchitis; asthmatic bronchitis; pneumonic diseases; pulmonary emphysema; chronic obstructive pulmonary disease; and acute respiratory distress syndrome (ARDS); and (2) inflammatory diseases selected from the group consisting of atopic dermatitis; conjunctivitis; urticaria; acquired immunodeficiency syndrome (AIDS); keloid formation; rhinitis; iridocyclitis; gingivitis; periodontitis; dentoalveolitis; gastritis; ulcerative colitis; Crohn's disease; gastrointestinal ulcer; esophagitis; myositis; encephalitis such as myasthenia gravis, multiple sclerosis and neuritis; hepatitis; scar tissue formation; nephritis including proliferative nephritis; peritonitis; pleurisy; scleritis; scleroderma; and scalds or burns.

23) The agent or drug according to any of the above 18) to 22) which is selected from the group consisting of oral pharmaceutical forms, injections and inhalants.

24) The agent or drug according to any of the above 18) to 22) which is selected from the group consisting of ointments, patches, solutions for external use, eyedrops, nose drops (collunaria) and suppositories.

The above objectives and other objectives, features, advantages, and aspects of the present invention are readily apparent to those skilled in the art from the following disclosures. It should be understood, however, that the description of the specification including the following best modes of carrying out the invention, examples, etc. is illustrating preferred embodiments of the present invention and given only for explanation thereof. It will become apparent to the skilled in the art that a great number of variations and/or alterations (or modifications) of this invention may be made based on knowledge from the disclosure in the following parts and other parts of the specification without departing from the spirit and scope thereof as disclosed herein. All of the patent publications and reference documents cited herein for illustrative purposes are hereby incorporated by reference into the present disclosure.

BEST MODES OF CARRYING OUT THE INVENTION

The present invention provides compounds, or salts thereof, having an unsubstituted or optionally substituted 5 to 6 membered heteroaryl group or a fused ring in which any of the heteroaryl groups is contained (for example, a fused benzene ring in which any of the heteroaryl groups is fused to a benzene ring), via a chain comprised of 1 to 8 members of methylene, on the position 3 of a 1,8-naphthyridin-2(1H)-one ring, which possess advantageous biological properties, and pharmaceutical compositions comprising at least one member selected from the aforementioned compounds and pharmaceutically acceptable salts thereof. The compounds or salts thereof are utilizable for their selective PDE IV-inhibiting actions. Therefore, the present invention also provides drugs for preventing and/or treating at least one member selected from diseases, disorders, and abnormal conditions related to an activity of PDE IV. It should be noted that any of 1,8-naphthyridin-2(1H)-one rings known in the art prior to the present case may be adoptable without any limitations wherein such 1,8-naphthyridin-2(1H)-one rings may have any of all substituents known to be placed on any of positions other than the position 3 of the 1,8-naphthyridin-2(1H)-one ring.

A preferred embodiment of the present invention is as follows:

The definitions for the compounds of the above-defined formula (1) will be given below in detail.

As used herein, the term "a 5 or 6 membered heteroaryl group or a fused benzene ring in which any of the above-defined heteroaryl groups is fused to a benzene ring" refers to a 5 or 6 membered heteroaryl group containing 1 or 2 heteroatoms selected from the group consisting of N, S, and O; or a fused benzene ring in which any of the above-defined heteroaryl groups is fused to a benzene ring. Representatives of such heteroaryl groups and fused benzene rings include pyrrolyl, pyridyl, 1-oxypyridyl, thienyl, furyl, imidazolyl, thiazolyl, oxazolyl, indolyl, quinolyl, benzothienyl, benzofuranyl, benzimidazolyl, benzothiazolyl, benzoxazolyl, etc. Among them, preferred groups include pyridyl, 1-oxypyridyl, thienyl, furyl, thiazolyl, and benzothiazolyl. Particularly, pyridyl and 1-oxypyridyl are preferable. Examples of the pyridyl are 2-pyridyl, 3-pyridyl, 4-pyridyl, etc.

The heteroaryl group and the fused benzene ring may be unsubstituted or optionally substituted with one or more substituents. The substituents include lower alkyl, lower alkoxy, hydroxyl, halogen, nitro, halogen-substituted lower alkyl, lower alkylthio, lower alkylsulfinyl, lower alkylsulfonyl, cyano, a residue derived from carboxylic acids and derivatives thereof, such as alkoxycarbonyl, and an amino nitrogen-containing radical such as di-lower alkylamino.

As used herein, the term "lower alkyl" refers to alkyl containing 1 to 4 carbon atoms, such as methyl, ethyl, propyl, and isopropyl.

The term "halogen" as used herein refers to fluorine, chlorine, bromine, and the like.

The term "lower alkylthio" refers to alkylthio containing 1 to 4 carbon atoms, such as methylthio, ethylthio, propylthio, and isopropylthio.

The term "lower alkylsulfinyl" refers to alkylsulfinyl containing 1 to 4 carbon atoms, such as methylsulfinyl, ethylsulfinyl, propylsulfinyl, and isopropylsulfinyl.

The term "lower alkylsulfonyl" refers to alkylsulfonyl containing 1 to 4 carbon atoms, such as methylsulfonyl, ethylsulfonyl, propylsulfonyl, and isopropylsulfonyl.

As used herein, the term "lower alkoxy" refers to alkoxy containing 1 to 4 carbon atoms, such as methoxy, ethoxy, propoxy, and isopropoxy.

Preferred compounds according to the present invention have the structural formula (1). Still more preferred compounds according to the present invention have the structural formula (1) wherein A is pyridyl or 1-oxypyridyl; and m is selected from 1 to 5.

Representative examples of compounds of the invention include the following:

1-(3-Nitrophenyl)-3-(pyridin-2-ylmethyl)-1,8-naphthyridin-2(1H)-one,
1-(3-Nitrophenyl)-3-(pyridin-3-ylmethyl)-1,8-naphthyridin-2(1H)-one,
1-(3-Cyanophenyl)-3-(pyridin-4-ylmethyl)-1,8-naphthyridin-2(1H)-one,
1-(3-Nitrophenyl)-3-(pyridin-4-ylmethyl)-1,8-naphthyridin-2(1H)-one,
1-(3-Nitrophenyl)-3-[2-(pyridin-2-yl)ethyl]-1,8-naphthyridin-2(1H)-one,
1-(3-Nitrophenyl)-3-[2-(pyridin-3-yl)ethyl]-1,8-naphthyridin-2(1H)-one,
1-(3-Nitrophenyl)-3-[2-(pyridin-4-yl)ethyl]-1,8-naphthyridin-2(1H)-one,
1-(3-Nitrophenyl)-3-[3-(pyridin-2-yl)propyl]-1,8-naphthyridin-2(1H)-one,
1-(3-Nitrophenyl)-3-[3-(pyridin-3-yl)propyl]-1,8-naphthyridin-2(1H)-one,
1-(3-Nitrophenyl)-3-[3-(pyridin-4-yl)propyl]-1,8-naphthyridin-2(1H)-one,
1-(3-Nitrophenyl)-3-[3-(1-oxypyridin-4-yl)propyl]-1,8-naphthyridin-2(1H)-one,
1-(3-Cyanophenyl)-3-[3-(pyridin-4-yl)propyl]-1,8-naphthyridin-2(1H)-one,
1-(3-Chlorophenyl)-3-[3-(pyridin-4-yl)propyl]-1,8-naphthyridin-2(1H)-one,
1-(3-Methylthiophenyl)-3-[3-(pyridin-4-yl)propyl]-1,8-naphthyridin-2(1H)-one,
1-(3-Methylsulfinylphenyl)-3-[3-(pyridin-4-yl)propyl]-1,8-naphthyridin-2(1H)-one,
1-(3-Methylsulfonylphenyl)-3-[3-(pyridin-4-yl)propyl]-1,8-naphthyridin-2(1H)-one,
1-(3-Methylsulfonylphenyl)-3-[3-(1-oxypyridin-4-yl)propyl]-1,8-naphthyridin-2(1H)-one,
7-Methyl-1-(3-nitrophenyl)-3-[3-(pyridin-4-yl)propyl]-1,8-naphthyridin-2(1H)-one,
7-Methyl-1-(3-methylthiophenyl)-3-[3-(pyridin-4-yl)propyl]-1,8-naphthyridin-2(1H)-one,
1-(3-Nitrophenyl)-3-[4-(pyridin-2-yl)butyl]-1,8-naphthyridin-2(1H)-one,
1-(3-Nitrophenyl)-3-[4-(pyridin-3-yl)butyl]-1,8-naphthyridin-2(1H)-one,
1-(3-Nitrophenyl)-3-[4-(pyridin-4-yl)butyl]-1,8-naphthyridin-2(1H)-one,
1-(3-Nitrophenyl)-3-[5-(pyridin-2-yl)pentyl]-1,8-naphthyridin-2(1H)-one,
1-(3-Nitrophenyl)-3-[5-(pyridin-3-yl)pentyl]-1,8-naphthyridin-2(1H)-one,
1-(3-Nitrophenyl)-3-[5-(pyridin-4-yl)pentyl]-1,8-naphthyridin-2(1H)-one
1-(3-Nitrophenyl)-3-[6-(pyridin-4-yl)hexyl]-1,8-naphthyridin-2(1H)-one,
1-(3-Nitrophenyl)-3-[7-(pyridin-4-yl)heptyl]-1,8-naphthyridin-2(1H)-one,
1-(3-Nitrophenyl)-3-[2-(2-thienyl)ethyl]-1,8-naphthyridin-2(1H)-one,
1-(3-Nitrophenyl)-3-[2-(3-thienyl)ethyl]-1,8-naphthyridin-2(1H)-one,
1-(3-Nitrophenyl)-3-[3-(2-furyl)propyl]-1,8-naphthyridin-2(1H)-one,
1-(3-Nitrophenyl)-3-[3-(3-furyl)propyl]-1,8-naphthyridin-2(1H)-one,
1-(3-Nitrophenyl)-3-[3-(thiazol-2-yl)propyl]-1,8-naphthyridin-2(1H)-one,
1-(3-Nitrophenyl)-3-[2-(benzothiazol-2-yl)ethyl]-1,8-naphthyridin-2(1H)-one,
1-(3-Nitrophenyl)-3-[3-(benzothiazol-2-yl)propyl]-1,8-naphthyridin-2(1H)-one,
1-(3-Nitrophenyl)-3-[4-(benzothiazol-2-yl)butyl]-1,8-naphthyridin-2(1H)-one,
1-(Pyridin-2-yl)-3-[3-(pyridin-4-yl)propyl]-1,8-naphthyridin-2(1H)-one,
1-(Pyridin-3-yl)-3-[2-(pyridin-4-yl)ethyl]-1,8-naphthyridin-2(1H)-one,
1-(Pyridin-3-yl)-3-[3-(pyridin-4-yl)propyl]-1,8-naphthyridin-2(1H)-one,
1-(Pyridin-3-yl)-3-[4-(pyridin-4-yl)butyl]-1,8-naphthyridin-2(1H)-one,
1-(Pyridin-4-yl)-3-[3-(pyridin-4-yl)propyl]-1,8-naphthyridin-2(1H)-one,
1-(Pyridin-3-yl)-3-[2-(benzothiazol-2-yl)ethyl]-1,8-naphthyridin-2(1H)-one, and
1-(Pyridin-3-yl)-3-[2-(benzothiazol-2-yl)propyl]-1,8-naphthyridin-2(1H)-one.

As used herein, "the compound(s) of the present invention" may include salts thereof, hydrates and solvates thereof, a variety of prodrug forms derived from functional groups existing in compound molecules. The prodrugs of the compounds according to the present invention include those compounds which can be transformed in vivo, for example, by metabolic processes, including hydrolysis, oxidation, reduction, trans-esterification, and the like, to yield the parent compounds of the formula (1), etc. Representatives of such prodrugs are ester-, amide-, ether-, amide-, alcohol-, and amine-derivatives thereof. Preferred compounds according to the present invention are potently active in the inhibition of IV-type phosphodiesterases.

Some of the compounds of formula (1) may exist in more than one tautomeric form. This invention extends to all tautomeric forms. The compounds of the instant invention may also contain one or plural asymmetric carbon atoms and thus give rise to optical isomers such as (R)- and (S)-isomers, racemates, diastereoisomers, etc. The present invention includes all such possible isomers, and their racemic and resolved, enantiomerically pure forms, as well as all mixtures thereof. The compounds of the invention may be isolated in the form of hydrates, solvates with, for example, ethanol and the like, and a variety of crystalline substances.

The present invention also encompasses pharmaceutically acceptable salts of the naphthyridine derivative having the formula (1). Such salts include those formed from any of medically or pharmaceutically utilizable non-toxic or low toxic inorganic or organic acids. Examples of the salts are hydrochloride, hydrobromate, sulfate, acetate, propionate, citrate, succinate, tartrate, methanesulfonate, p-toluenesulfonate, etc.

The compounds of the present invention can be prepared by one of various routes. For instance, the compounds of the formula (1) can be prepared by one of the following schemes or modifications thereof:

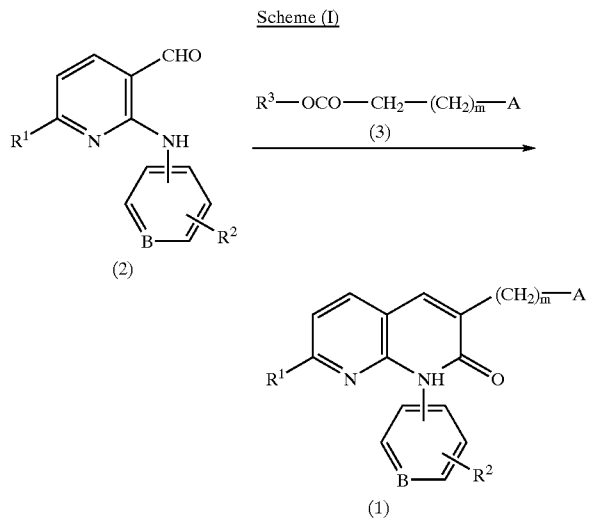

In the aforementioned Scheme, the compounds of the formula (1) wherein A, B, $R^1$, $R^2$ and m, all have the meanings given above can be prepared by condensing a compound of the formula (2) wherein B, $R^1$ and $R^2$, all have the meanings given above with a compound of the formula (3) wherein $R^3$ is lower alkyl, and m and A, both have the meanings given above in the presence of a base.

In the compounds of the formula (3), the lower alkyl for $R^3$ has the same meaning as in the above-defined compounds of the formula (1) and refers to alkyl containing 1 to 4 carbon atoms, such as methyl, ethyl, propyl, and isopropyl.

Bases used in this condensation may include alkali metal amides, alkali metal hydrides, alkyl lithium, aryl lithium, and the like. Examples of the base are lithium diisopropylamide (LDA), sodium bistrimethylsilylamide, potassium hydride, methyl lithium, phenyl lithium, etc. The reaction can be conducted in the presence of or in the absence of a solvent. When the reaction is conducted in solvents, it is often convenient to use conventional solvents which are free from any adverse action on the reaction. Preferred examples of such solvents are tetrahydrofuran (THF), diethyl ether, methylene chloride, etc. The reaction temperature range is about −80 to 100° C. and preferably about −80° C. to room temperature.

In the aforementioned Scheme (I), the compounds of the formula (2) can be prepared by one of known methods (e.g., JP, A, 62-158281 (1987); JP, A, 62-228076 (1987); etc.) or modifications thereof.

In the aforementioned Scheme (I), the compounds of the formula (3) can be prepared, for example, by one of the synthetic routes described herein. The disclosures given below illustrate the preparation of compounds of the formula (3) wherein A is pyridyl. For instance, the compounds of the formula (3) wherein A is pyridyl and m is 1, 2 or 3, can be prepared according to one of Schemes (IIa), (IIb) and (IIc) outlined as follows:

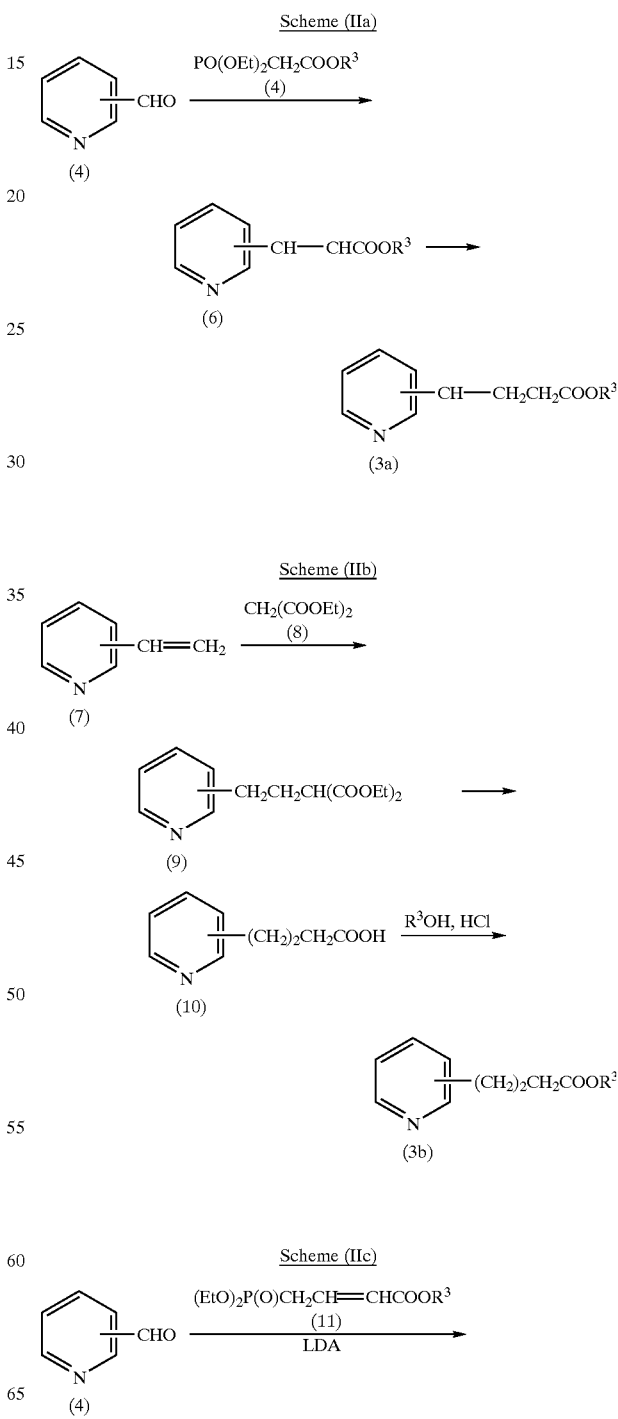

-continued

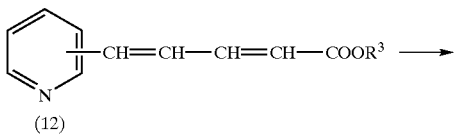

(12)

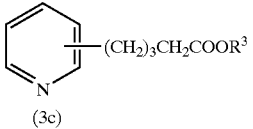

(3c)

Described below is an illustration for each production process.

Scheme (IIa)

A pyridylacrylic acid ester (6) can be prepared by condensing a pyridine aldehyde (4) with a diethylphosphono acetic acid lower alkyl ester of the formula (5) wherein $R^3$ has the same meaning as defined above in the presence of a base such as sodium hydride. Next, a compound of the formula (3) wherein A is pyridyl and m is 1 (Compound (3a)) can be prepared by reduction of the compound (6). The reduction of the compound (6) can be effected generally by hydrogenation in the presence of a suitable catalyst such as palladium on carbon.

Scheme (IIb)

A compound (9) can be prepared by addition of ethyl malonate (8) to vinylpyridine (7) in the presence of a suitable base such as sodium methoxide or sodium ethoxide. Next, the compound (9) can be hydrolyzed under acidic conditions (for example, with conc. hydrochloric acid) and then decarboxylated to give a carboxylic acid derivative (10). A compound of the formula (3) wherein A is pyridyl and m is 2 (Compound (3b)) can be prepared by esterification of the carboxylic acid derivative (10) with a lower alkyl alcohol of the formula: $R^3OH$ wherein $R^3$ has the same meaning as defined above. It should be noted that the aforementioned compounds (3b) may be prepared by processes entirely different from the Scheme (IIb), i.e., they can be prepared according to the procedure of Synthetic Example 7 given below.

Scheme (IIc)

A compound (12) can be prepared by condensing a pyridine aldehyde (4) with a diethylphosphonocrotonic acid lower alkyl ester of the formula (11) wherein $R^3$ has the same meaning as defined above in the presence of a base such as LDA. Next, a compound of the formula (3) wherein A is pyridyl and m is 3 (Compound (3c)) can be prepared by reduction (for example, catalytic reduction) of the compound (12). In this Scheme, the catalytic reduction may be effected by techniques similar to the reduction in the Scheme (IIa).

The compounds of the formula (3) wherein A is pyridyl and m is selected from 4 to 8 (Compound (3d)), can be prepared according to the Scheme (IId) outlined as follows:

Scheme (IId)

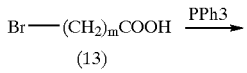

-continued

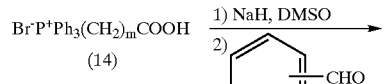

3) $ClCH_2CN$

(15)

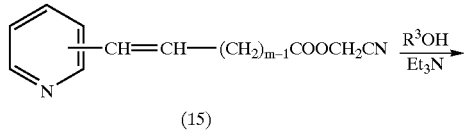

(16)

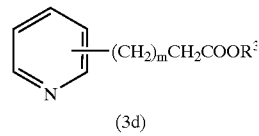

(3d)

wherein m is an integer selected from 4 to 8, both inclusive.

A bromoalkyl carboxylic acid (13) is reacted with triphenylphosphine to produce a phosphonium salt (14) which is then treated with a base prepared from sodium hydride and dimethylsulfoxide (DMSO) to give a phosphorane. The resultant phosphorane is reacted with a pyridine aldehyde (4) followed by treatment with chloroacetonitrile. The resulting cyanomethyl ester derivative (15) is subjected to a trans-esterification using a lower alkyl alcohol of the formula: $R^3OH$ wherein $R^3$ has the same meaning as defined above in the presence of a catalytic amount of triethylamine to produce a lower alkyl ester derivative (16) which is then reduced to give a compound of the formula (3) wherein A is pyridyl and m is selected from 4 to 8 (Compound (3d)). It should be noted that the reduction of the lower alkyl ester derivative (16) may be conducted by techniques similar to the catalytic reduction in the Scheme (IIa).

The aforementioned Schemes (IIa) to (IId) and suitable modifications thereof are adoptable for preparing compounds of the formula (3) wherein A is a 5 or 6 membered heteroaryl group or a fused benzene ring in which any of the heteroaryl groups is fused to a benzene ring, other than pyridyl. For the Scheme (I), it should be noted that the compounds of the formula (3) wherein A is benzothiazolyl can be prepared according to methods known to those skilled in the art (e.g., JP, A, 8-208631 (1996), etc.).

The compounds of the present invention so prepared may be isolated or purified as free forms per se or in the form of salts after being subjected to conventional salt-forming treatments. The isolation and purification can be effected by adaptations of ordinary chemical operations including, for example, extraction, concentration, distillation, crystallization, filtration, recrystallization, various chromatographic techniques, etc. various isomers can be separated by conventional methods utilizing a difference of physico-chemical properties among such isomers. For example, stereochemically pure isomers can be obtained from racemic mixtures by an ordinary racemic resolution (for example, by first converting said racemic mixtures with usual optically-active acids (including tartaric acid, etc.) to diastereomer salts followed by optical resolution, etc.). Diastereomers can be separated by ordinary methods such as selective crystallization or chromatographic techniques.

Pure optically-active isomeric forms of the compounds of the present invention may also be obtained from the pure optically-active isomeric forms of the appropriate starting materials and intermediates.

The compounds of the present invention are potent inhibitors of PDE IV. The compounds of the present invention are thus of use in the prophylaxis and treatment of diseases and abnormal states related to PDE IV actions. In particular, the compounds of the present invention are effective as prophylactic or therapeutic agents for diseases and conditions associated with an abnormal enzymatic or catalytic activity of PDE IV. The compounds of the present invention are of use in medicine, especially in the prophylaxis and treatment of:

(1) respiratory diseases, including, for example, bronchial asthma (including chronic bronchial asthma and atopic asthma), acute bronchitis, chronic bronchitis, asthmatic bronchitis, pneumonic diseases, pulmonary emphysema, chronic obstructive pulmonary disease (COPD), acute respiratory distress syndrome (ARDS), and the like;

(2) inflammatory diseases, including, for example, atopic dermatitis, conjunctivitis, urticaria, acquired immunodeficiency syndrome (AIDS), keloid formation, rhinitis, iridocyclitis, gingivitis, periodontitis, dentoalveolitis, gastritis, ulcerative colitis, Crohn's disease, gastrointestinal ulcer, esophagitis, myositis, encephalitis (such as myasthenia gravis, multiple sclerosis and neuritis), hepatitis, scar tissue formation, nephritis (including proliferative nephritis), peritonitis, pleurisy, scleritis, scleroderma, scalds or burns, and the like;

(3) systemic or local joint diseases, including, for example, osteoarthritis, gouty arthritis, rheumatoid arthritis, malignant rheumatism, psoriatic arthritis, and the like;

(4) inflammatory conditions associated with organ transplantation, etc., including, for example, reperfusion injury, graft versus host reaction, and the like;

(5) diseases or symptoms related to urination, including, for example, diabetes insipidus, urethritis, urinary incontinence, cystitis, irritable bladder, neurogenic bladder, uremia, uriniferous tubular disorder, pollakiuria, ischuria, and the like;

(6) diseases or abnormal conditions related to tumor necrosis factor (TNF) (for example, TNF-α, etc.) and other cytokines (for example, IL-1, IL-4, IL-6, etc.), including, for example, psoriasis, rheumatoid arthritis, ulcerative colitis, Crohn's disease, septicemia, septic shock, endotoxic shock, gram-negative bacillus sepsis, toxic shock syndrome, nephritis, hepatitis, infection (induced by bacteria and viruses), circulatory failure (heart failure, arteriosclerosis, myocardial infarction, cerebral apoplexy), and the like;

(7) proliferative diseases, including, for example, malignant tumors, leukemia, proliferative dermal diseases (keratosis and various types of dermatitides), connective tissue diseases and the like;

(8) diseases related to nervous function abnormality, including, for example, impaired learning, memory and recognition associated with neurodegenerative disorders such as Alzheimer's disease and Parkinson's disease, multiple lateral sclerosis, senile dementia, amyotrophic lateral sclerosis, acute demyelinating neuritis, muscular dystrophy, and the like;

(9) diseases related to abnormality of mental functions, including, for example, manic-depressive psychosis, schizoid, anxiety, panic, and the like;

(10) diseases demanding protection of nerves and cells, including, for example, cardiac arrest, spinal cord injury, intermittent claudication, ischemic diseases (including, for example, angina pectoris, cardiac infarction, cerebral apoplexy, head injury, etc.) and the like;

(11) endocrine diseases, including not only diabetes but also diabetic retinopathy, diabetic nephropathy, diabetic neurosis, amyloidosis, pancreatitis, thyroiditis, obesity, prostatomegaly, and the like;

(12) autoimmune diseases, including, for example, systemic lupus erythematosus (SLE), atrophic gastritis, thyroid diseases, glomerular nephritis, orchitis, adrenal diseases, hemolytic anemia, oophoritis, and the like;

(13) cardiovascular diseases, including, for example, hypertension, angina pectoris, heart failure, myocarditis, external epicarditis, endocarditis, valvulitis, and the like;

(14) vessel and blood system diseases, including, for example, angiitis, aneurysm, endoangiosis, thromboangiitis, granulomatosis, cerebrovascular angiitis, arteriosclerosis, periangitis, leukopenia, thrombocytopenia, Boeck's sarcoid, and the like;

(15) diseases related to immune reactions or allergic responses, including, for example, contact dermatitis, serum sickness, drug allergy, Goodpasture's syndrome, lymphoma, rheumatic fever, AIDS, anaphylactic shock and the like; and

(16) other diseases, disorders or abnormal states, including, for example, glaucoma, spastic paralysis, impotence, diseases or illness accompanied with pain (contusion, headache, etc.), neck-shoulder-arm syndrome, nephropathy, renal insufficiency, hepatic insufficiency, obesity, etc. It is known that the aforementioned diseases and abnormal conditions would be related to an activity of PDE IV.

Particularly, the compounds of the present invention act as prophylactic and/or therapeutic drugs for:

(a) respiratory diseases (including, for example, bronchial asthma including chronic bronchial asthma and atopic asthma; acute bronchitis; chronic bronchitis; pneumonic diseases; pulmonary emphysema; chronic obstructive pulmonary disease; acute respiratory distress syndrome (ARDS); etc.);

(b) inflammatory diseases (including, for example, atopic dermatitis; conjunctivitis; urticaria; acquired immunodeficiency syndrome (AIDS); keloid formation; rhinitis; iridocyclitis; gingivitis; periodontitis; dentoalveolitis; gastritis; ulcerative colitis; Crohn's disease; gastrointestinal ulcer; esophagitis; myositis; encephalitis (e.g., myasthenia gravis, multiple sclerosis and neuritis); hepatitis; scar tissue formation; nephritis including proliferative nephritis; peritonitis; pleurisy; scleritis; scleroderma; scalds or burns; etc.); and (c) diseases or abnormal conditions related to tumor necrosis factor (TNF) and other cytokines (e.g., IL-1, IL-6, etc.) (including, for example, psoriasis, rheumatoid arthritis, ulcerative colitis, Crohn's disease, septicemia, septic shock, endotoxic shock, gramnegative bacillus sepsis, toxic shock syndrome, nephritis, hepatitis, infection (induced by bacteria and viruses), circulatory failure (e.g., heart failure, arteriosclerosis, myocardial infarction, cerebral apoplexy, etc.), and the like).

More preferably, the compounds of the present invention act as drugs for preventing and/or treating at least one disease or abnormal state selected from respiratory diseases (including, for example, bronchial asthma including chronic bronchial asthma and atopic asthma; acute bronchitis; chronic bronchitis; pneumonic diseases; pulmonary emphysema; chronic obstructive pulmonary disease; acute respiratory distress syndrome (ARDS); etc.). Among them, the compounds of the present invention are most preferably effective as prophylactic and/or therapeutic drugs for bronchial asthma.

The compounds of the present invention are particularly useful in treating or preventing diseases or abnormal states because they are significantly less emetic than the prior art PDE IV inhibitors. The compounds of the present invention are effective in treating or preventing diseases or abnormal states wherein they are required to be administered systemically or locally.

Thus, the present invention encompasses pharmaceutical compositions comprising an effective amount of at least one member selected from the above-defined compounds (1) and pharmaceutically acceptable salts thereof, and not only inhibitors of PDE IV but also pharmaceutical drugs for preventing or treating at least one member selected from diseases and abnormal conditions related to an activity of PDE IV, more preferably anti-asthmatic agents.

As aforementioned, since PDE IV is predominantly in vivo located in airway smooth muscle cells and inflammatory cells, the compounds of the present invention inhibit selectively PDE IV in these cells, thereby exerting a bronchodilator action via relaxing airway smooth muscles, together with an anti-inflammatory action through suppressing inflammatory cell activation. Hence, the compounds of the present invention are widely effective in ameliorating a variety of undesirable responses and symptoms raised with regard to asthma.

The following disclosure is to illustrate an anti-asthmatic efficacy of the compounds of the present invention in detail:

It is known that a series of responses, such as an immediate asthmatic response, a delayed asthmatic response, and a hypersensitive airway response, are induced when an asthmatic patient inhales antigens which cause the disease.

First, the immediate asthmatic response that begins immediately after inhalation of antigens is a typical airway smooth muscle constrictive reaction induced by chemical mediators (including histamine, leukotrienes, etc.) which are released from mast cells as a result of antigen-antibody interactions. Later the delayed asthmatic response is observed, which occurs within 4 to 24 hours after the inhalation of antigens. For its pathological states, an infiltration of inflammatory cells into lung tissues, airway mucosa edema, etc. are observed. Thereafter, the hypersensitive airway response is further elicited, which occurs within 1 to 14 days after the inhalation of antigens and is a state wherein the airway reactivity is increased. In such a stage, even quite mild stimuli lead to constriction of the airway and occurrence of serious airway obstruction.

As aforementioned, various responses and symptoms appear in asthma. The compounds of the present invention can exert an excellent inhibitory and/or ameliorating activity on such responses and symptoms at each stage, relying on their bronchodilator and anti-inflammatory actions based on the inhibition of PDE IV.

In addition, since the PDE-inhibiting action exerted by the compounds of present invention is highly selective against PDE IV but less selective for other isoenzymes located in certain tissues such as CNS and heart, it may be possible to avoid side-effects (for example, spasm, tachycardia, palpitation, etc.) caused by the inhibition of these isoenzymes when the present invention is applied.

Diseases and abnormal states to be targeted by the therapy using the compounds of the present invention include the aforementioned diseases and abnormal conditions, preferably diseases and abnormal conditions accompanied with respiratory dysfunctions and inflammation at the area of bronchus and airway. Embodiments of such diseases include bronchial asthma, chronic bronchial asthma, acute bronchitis, chronic bronchitis, asthmatic bronchitis, pulmonary emphysema, and other bronchus and airway inflammatory states, etc. It is noted that chronic bronchitis and pulmonary emphysema may also be generically termed chronic obstructive pulmonary disease.

For patients with the foregoing diseases, disorders, and abnormal states, the compounds of the present invention can be used independently without any additives, but preferably in admixture with any of pharmaceutically acceptable additives. The compounds of the present invention may be orally, parenterally (including by injection), topically (including by inhalation) administered as pharmaceutical compositions or formulations. One or more components selected from known pharmaceutical additives (hereinafter also referred to "pharmaceutical ingredient(s)") can be employed in the aforementioned pharmaceutical compositions or formulations for any of administration routes. Embodiments of such known pharmaceutical additives may be suitably selected, according to administration routes and applications of pharmaceutically formulated forms, from components as disclosed in, for example, (1) "Iyakuhin Tenkabutsu Handbook (Handbook of PHARMACEUTICAL EXCIPIENTS)", Maruzen Publishing Company, Japan (1989);

(2) "Iyakuhin Tenkabutsu Jiten (Pharmaceutical Excipient Dictionary)", First Edition, K.K. Yakuji Nippo Sha, Japan (1994);

(3) "Iyakuhin Tenkabutsu Jiten Tsuiho (Pharmaceutical Excipient Dictionary, Supplement)", First Edition, K.K. Yakuji Nippo Sha, Japan (1995); and (4) "Yakuzaigaku (Pharmaceutics)", 5th Edition, K.K. Nankodo, Japan (1997).

For oral administration, the aforementioned additives are any pharmaceutical ingredients as long as they are suitable for oral drugs and the intended purposes according to the present invention. Usually, the pharmaceutical additive is selected from conventional pharmaceutical ingredients such as vehicles, binders, disintegrants, lubricants and coating agents. The oral formulations of the present invention include tablets, capsules, granules, fine granules, powders, syrups, etc. The oral drug includes controlled-release system preparations wherein the in vivo release of the compound of the present invention which is contained as the active ingredient is controlled using any of known pharmaceutical ingredients (for example, immediate-release preparations, sustained-release preparations, etc.). The aforementioned oral drug may include enteric preparations. In some cases, it is rather preferable that the oral drugs are prepared in the form of such enteric preparations. Such enteric preparations include coated or matrix formulations using any of enteric coating agents such as cellulose phthalate, hydroxypropyl methylcellulose phthalate, and methyl methacrylate-methacrylic acid copolymers, among the coating agents given below, and capsule formulations wherein any of the enteric coating agents is contained as an ingredient for their coat.

Embodiments of pharmaceutical ingredients as used for the aforementioned oral drugs are listed below but not limited to:

1) representatives of fillers:
lactose, starch (including corn starch), crystalline cellulose, microcrystalline cellulose, crystalline cellulose-carboxymethylcellulose sodium, dextrin, sucrose, glucose, mannitol, calcium carbonate, calcium phosphate, calcium sulfate, calcium silicate, Crosspovidone, dried yeast, and soybean oil unsaponifiable fractions;

2) representatives of binders:
starch (including corn starch), gelatin, gum acacia, hydroxypropyl cellulose (HPC), methylcellulose (MC), carboxymethylcellulose (CMC), polyvinyl-pyrrolidone (PVP), ethylcellulose (EC), glucose, and sucrose;

3) representatives of disintegrants:
starch (including corn starch), agar, gelatin, CMC—Na, CMC—Ca, crystalline cellulose, crystalline cellulose-carboxymethylcellulose sodium, low-substituted HPC, Crosspovidone, calcium carbonate, and sodium bicarbonate;

4) representatives of lubricants:
magnesium stearate, hydrogenated vegetable oil, talc, Macrogol, and light anhydrous silicic acid; and 5) representatives of coating agents:
sucrose, HPC, shellac, gelatin, glycerin, sorbitol, EC, HPC, hydroxypropyl methylcellulose (HPMC), PVP, cellulose acetate phthalate (CAP), hydroxypropyl methylcellulose phthalate (HPMCP), methyl methacrylate-methacrylic acid copolymers, and titanium oxide.

For injection, the additives include pharmaceutical ingredients suitable for aqueous or non-aqueous injections. Usually, the additive is selected from conventional pharmaceutical ingredients such solubilizers, solution adjuvants, suspending agents, buffers (pH regulators), stabilizers and preservatives. In addition, it may be selected from conventional ingredients suitable for preparing powders for injection, which are used in solution or suspension when administered.

Representatives of said solubilizers for injections include water for injection, physiological saline, Ringer's solution, vegetable oil (for example, olive oil, sesame oil, soybean oil), ethanol, propylene glycol, polyethylene glycol, glycerin, N,N-dimethylacetamide, N-methyl-2-pyrrolidone, etc. Representatives of said solution adjuvants, suspending agents, buffers (pH regulators), stabilizers and preservatives for injections include polyethoxylated hydrogenated castor oil, ethylene diamine, benzyl alcohol, Polysorbate 80, carboxymethylcellulose sodium, sodium hydroxide, sodium citrate, sodium acetate, potassium dihydrogen phosphate, sodium hydrogen sulfite, ascorbic acid, methyl parahydroxybenzoate, propyl parahydroxybenzoate, chlorobutanol, etc. Representatives of said constituents for powdered injections include glucose, sorbitol, etc.

When administered topically, for example, via inhalation, etc., the aforementioned additives as used herein include any of pharmaceutical ingredients known in the art, such as solution adjuvants, stabilizers, buffers, suspending agents, emulsifying agents, and preservatives. Embodiments of inhalants include aerosols. Aerosol-producing techniques are any of types including a spraying type wherein active drug ingredients are packed together with propellants such as fluorocarbon alternatives into a sealed container and sprayed, and a nebulizer or atomizer type using a pressured gas, such as carbon dioxide and nitrogen, filled in a container different from that for active drug ingredients.

For said aerosols, representatives of pharmaceutical ingredients such as propellants, solution adjuvants, stabilizers, buffers, suspending agents, emulsifying agents, and preservatives, include chlorine-free fluorinated hydrocarbons [e.g., 1,1,1,2-tetrafluoroethane (HFA-134a), 1,1,1,2,3,3,3-heptafluoropropane (HFA-227), etc.], alcohol, propylene glycol, polyethylene glycol, Polysorbate 80, glycerin, egg yolk lecithin, soybean lecithin, α-tocopherol, ascorbic acid, benzalkonium chloride, chlorobutanol, etc. Besides, when the aerosols are prepared in the form of nebulizers or atomizers as aforementioned, the pharmaceutical ingredients as used may include water for injection, purified water, etc. Further, the inhalants may also be prepared in the form of not only sprays wherein any of the above-defined propellants is used, nebulizers or atomizers, but also powders. Such powder inhalants can be in any of forms similar to available powder inhalants in the art (e.g., INTAL (registered trademark) capsule and metered-dose inhaler: SPINHALER (registered trademark); for administration of sodium chromoglicate).

In addition to the aforementioned inhalants, the compounds of the present invention may be administered topically in the form of ointments, transdermic patches, solutions for external use, eyedrops, nose drops or suppositories. Such topical pharmaceutical preparations may suitably contain pharmaceutical ingredients as disclosed in the aforementioned "Iyakuhin Tenkabutsu Handbook (Handbook of PHARMACEUTICAL EXCIPIENTS)", "Iyakuhin Tenkabutsu Jiten (Pharmaceutical Excipient Dictionary)", etc.

Desired oral drugs, injections or drugs for topical applications (including inhalants) comprising the compound of the present invention in admixture with the aforementioned ingredient can be prepared according to manufacturing methods known per se, for example, those described in The 13th Pharmacopoeia of Japan (JPXIII) or appropriately modified ones.

The pharmaceutical compositions (drugs) of the present invention are administered to mammals, particularly including human. The doses of these compounds or salts thereof are usually about 0.1 to 1,000 mg (per day), preferably about 0.1 to 500 mg (per day) for oral administration; usually about 0.01 to 200 mg (per day), preferably about 0.05 to 100 mg (per day) for injection; and usually about 0.01 to 200 mg (per day), preferably about 0.05 to 100 mg (per day) for topical applications. specific administration routes and dose levels (including the optimal dose) for any particular patient will be employed depending upon a variety of factors including the patient's conditions (general health, the severity of the particular disease or symptom undergoing therapy, the presence or absence of complications thereof, etc.), the age, sex, body weight, and the like.

EXAMPLES

Described below are examples, including assay examples, synthetic examples and formulation examples, of the present invention which are provided only for illustrative purposes, and not to limit the scope of the present invention. All the examples were carried out or can be carried out, unless otherwise disclosed herein specifically, by standard techniques which are well known and conventional to those skilled in the art.

Assay Examples

Described below are examples of pharmacological assays for the efficacy and safety of the compounds (1) of the present invention wherein their protocols and results are provided.

Assay Example 1

PDE Inhibition

Protocol

The assays for PDE activity were conducted according to Nicholson et al. method (Br. J. Pharmacol., 97, 889 (1989)).

Among PDE isozymes, type I, II, III and IV PDEs as used herein were separated from porcine hearts by using an anion exchange chromatography. Type V PDE was also separated from porcine aortae with an anion exchange chromatography and used herein.

Each PDE isozyme was admixed with ethylene glycol (EG) to adjust the final EG concentration to 30%, then stored at −20° C. and diluted when used. The enzymatic activity for PDE I and V was measured using cGMP as a substrate while that for POE II, III and IV was measured using cAMP.

[$^3$H]-cAMP (962 GBq/mmol; Amersham, 25 μl (100,000 cpm)) or [$^3$H]-cGMP (962 GBq/mmol; Amersham, 25 μl (100,000 cpm)) was added together with each PDE isozyme (25 μl) to an incubation buffer solution with the composition given below to adjust the total volume to 250 μl. Each test compound was dissolved in DMSO to adjust the final concentration to 1% (2.5 μl/tube).

Incubation buffer solution (pH7.5):

Tris-HCl (50 mM), magnesium chloride (6 mM), dithiothreitol (2.5 mM), 5-nucleotidase (4 μg/ml), bovine serum albumin (0.23 mg/ml), and cAMP (1 μM) [or cGMP (1 μM)]

A mixture of the aforementioned test compound solution and the buffer solution was incubated at 30° C. for 20 minutes. The reaction was quenched by admixing with 1 ml of anion exchange resin slurry (AG1-X8, 200–400 meshes, chloride form; Bio-Rad) to absorb unreacted substrates.

After the reaction stopped, the mixture was centrifuged at 200×g for 10 minutes, and the resulting supernatant was collected with vials in 250 μl aliquots. To each vial was added 5 ml of ACS-II (scintillator, Amersham). The radioactivity was measured with a liquid scintillator counter for [$^3$H]-adenosine or [$^3$H]-guanosine and set as the PDE activity. The measurements were conducted under conditions wherein the enzymatic activity was elevated by adding calmodulin (20 U/ml; Amersham) and calcium chloride (0.1 mM) for PDE-I and cGMP (1 μM) for PDE II, respectively.

The % inhibition was calculated for test compounds, and IC$_{50}$ (the concentration of each test compound required for 50% inhibition) was obtained by Probit method. The results are shown in Table 1. The aforementioned rolipram ((−)-isomer, optical purity: 91% e.e.) known as the PDE IV inhibitor in the prior art was used for the reference compound in this assay.

Further, for a comparison with compounds as disclosed in JP, A, 63-159382 (1988), the PDE-inhibiting activity was also measured for Compounds A and D in Table 1 of JP, A, 63-159382 (1988).

TABLE 1

| | Inhibition of PDE Isoenzymes (IC$_{50}$; μM) | | | | |
|---|---|---|---|---|---|
| Test Compounds | I | II | III | IV | V |
| Example No. 2 | >100 | >100 | >100 | 0.11 | 16 |
| Example No. 3 | >100 | >100 | >100 | 1.2 | 3.9 |
| Example No. 5 | 22 | >100 | 60 | 0.06 | 13 |
| Example No. 6 | >100 | >100 | >100 | 0.16 | 15 |
| Example No. 7 | >100 | >100 | >100 | 1.3 | 4.7 |
| Example No. 8 | >100 | >100 | >100 | 0.44 | >100 |
| Example No. 10 | >100 | 52 | 24 | 1.5 | 13 |
| Example No. 13 | 62 | 60 | 94 | 1.2 | 13 |
| Example No. 14 | 83 | 85 | 59 | 1.5 | 5.1 |
| Example No. 15 | 100 | 47 | 49 | 1.4 | 8.7 |
| Example No. 16 | 98 | 63 | 69 | 1.9 | 7.4 |
| Example No. 17 | >100 | >100 | >100 | 2.2 | >100 |

TABLE 1-continued

| | Inhibition of PDE Isoenzymes (IC$_{50}$; μM) | | | | |
|---|---|---|---|---|---|
| Test Compounds | I | II | III | IV | V |
| Example No. 23 | >100 | >100 | >100 | 1.2 | >100 |
| Rolipram | >100 | >100 | >100 | 0.78–3.2 | >100 |

Conclusion

As seen in Table 1, it has been ascertained that the compounds of the present invention inhibit selectively PDE IV.

In contrast, although Compound A and D seem to be selective for PDE IV, the IC$_{50}$ values of the compounds for PDE IV inhibition are merely 8.5 μM and 9.2 μM, respectively. Accordingly, it has been ascertained that the compounds of the present invention are significantly advantageous over these prior art compounds in view of PDE IV-inhibitory actions.

Assay Example 2

Inhibition of Antigen-Induced Immediate Asthmatic Response (Anti-Asthmatic Action)

Protocol (1) Active Sensitization of Guinea Pigs

Male Hartley outbred guinea pigs were sensitized by administering intraperitoneally physiological saline (0.5 ml) containing ovalbumin (1 mg, antigen) and 5×10$^9$ inactivated *Bordetella pertussis* dead cells (adjuvant).

Eleven to thirteen days after the first sensitization, 0.05 ml of an ovalbumin solution (1 mg/ml) (ovalbumin is dissolved in physiological saline) was administered to the lateroabdominal region of each guinea pig intracutaneously. An establishment of sensitization was checked relying on cutaneous reaction. Only guinea pigs wherein significant reddening responses occurred 5 to 10 minutes later were employed in the next measurement test for airway resistance.

(2) Measurement for Airway Resistance in Actively Sensitized-Guinea Pigs

The guinea pigs (3 animals per group) actively sensitized in the above step (1) were employed to measure for their airway pressure according to Konzett-Rossler method (Arch. Exp. Path. Pharmakol., 195, 71 (1940)).

Thirteen days after the final sensitization, guinea pigs fasted overnight, and were on the next day anesthetized with a pentobarbital solution (60 mg/1.2 ml/kg, dissolved in physiological saline, intraperitoneal administration). After the guinea pigs were fixed in a supine position, their trachea was incised followed by insertion with one port of a 4-port cannula. Among the remaining 3 ports, 2 ports were connected to an artificial respirator (Model 683, Harvard). The animals were ventilated with 10 ml/kg of air per ventilation at a rate of 60 beats/min via the artificial respirator from the cannula. One port remainder was connected to a respiratory amplifier (AR-601G, Nihon Kohden, Japan) via an airflow resistance tube (TV-241T, Nihon Kohden, Japan) and a differential pressure transducer (TP-602T, Nihon Kohden, Japan) connected with a control box (RY-111S, Nihon Kohden, Japan). From a catheter inserted into a left carotid artery, blood pressures were monitored with a blood pressure measurement unit (AP641G, NEC Corp., Japan) via a blood pressure transducer (TP-300T, Nihon Kohden, Japan), and heart rates were recorded on a thermal recorder (WT-685G, Nihon Kohden, Japan), relying on blood pressure pulse waves after being led to a cardiograph unit (AT601G, Nihon Kohden, Japan).

After airway pressure became stable, an ovalbumin solution (1 mg/ml, dissolved in physiological saline) was administered at a dose of 1 ml/kg via a tube with which the right jugular vein of guinea pigs was cannulated. Each area under airway pressure-time curve (AUC) was obtained by measuring amplitudes of the airway pressure prior to the antigen-challenge, 1, 2, 3, 4, 5, 10, 15 and 20 minutes post-challenge, and each percent increase (%) in airway resistance was further calculated according to the following equation:

$$\text{Percent Increase (\%) in Airway Resistance} = \left( \frac{AUC \text{ for 20 min after Antigen-Challenge}}{\text{Basal Respiratory Pressure}} - 1 \right) \times 100$$

Each test compound was suspended in 0.5% CMC—Na solution and administered orally with an oral sound at a dose of 3 mg/2 ml/kg 60 minutes prior to the antigen-challenge. Control groups received only 0.5% CMC—Na solution in an equivalent amount. The pentobarbital-anesthetization and tracheal incision were conducted 30 minutes prior to the antigen-challenge.

Each percent reduction of increase in airway resistance (each test compound-administered group versus control group) was calculated according to the equation given below. The results are shown in Table 2 wherein each value is an average of 3 animals. Rolipram as described in Assay Example 1 was used for the reference compound in this assay.

$$\text{Percent Reduction (\%) of Increase in Airway Resistance} = 100 - \left( \frac{\text{Percent Increase in Airway Resistance (Test Compound-Administered Group)}}{\text{Percent Increase in Airway Resistance (Control Group)}} \right) \times 100$$

TABLE 2

| Test Compounds | % Reduction of Increase in Airway Resistance (3 mg/kg, orally) |
| --- | --- |
| Example No. 2 | 64 |
| Example No. 5 | 90 |
| Example No. 6 | 87 |
| Example No. 7 | 95 |
| Example No. 8 | 88 |
| Example No. 10 | 82 |
| Example No. 14 | 92 |
| Example No. 16 | 96 |
| Example No. 23 | 90 |
| Rolipram | 58 to 92 |

Conclusion

As seen in Table 2, it has been ascertained that the compounds of the present invention reverse an increase in airway resistance as much as or greater than rolipram does and exert an excellent inhibitory action on antigen-induced immediate asthmatic responses.

These are also supported by the following assay results:

For a comparison with compounds as disclosed in JP, A, 63-159382 (1988), the percent reduction of increase in airway resistance was obtained for the compounds of the present invention (oral administration at a dose of 1 mg/kg), the compounds in Table 1 of JP, A, 63-159382 (1988) (oral administration at a dose of 1 mg/kg), and rolipram (reference compound; oral administration at a dose of 3 mg/kg), respectively, in the same assay manner as in the aforementioned Assay Example 2.

As a result, the compounds of the present invention, i.e., Example No. 5 Compound and Example No. 8 Compound, exert 86% and 88% reductions, respectively, of increase in airway resistance.

In contrast, Compounds A and D (JP, A, 63-159382 (1988), Table 1) are merely 68% and 70%, respectively, for the reduction of increase in airway resistance. Rolipram's percent reduction of increase in airway resistance is only 65%. Accordingly, it has been ascertained that the compounds of the present invention reverse an increase in airway resistance more excellently than the compounds as disclosed in JP, A, 63-159382 (1988).

Assay Example 3

Toxicology Study

Protocol

Each Compound (Example Nos. 8 and 10) was administered orally to CD (SD) rats (5 animals per group) as a test compound once a day for 4 successive weeks in a forced manner. The rats were observed for the time course of their general health conditions and measured for their body weight. When the administration was brought to an end, organs were weighed, and main organs were further examined pathohistologically.

Each test compound was suspended in 0.5% CMC—Na solution and given orally to the animal at a dose of 1 mg/5 ml/kg or 5 mg/5 ml/kg in a forced manner.

Conclusion

None of the animals were died in every dose group when the test compounds were administered. No reduction of body weight gains was observed, either. Further, no abnormality was observed for other parameters.

Assay Example 4

Emetic Action

Protocol

Female beagles (each group consisting of 3 dogs) as used herein were fed. One hour later, a suspension of each test compound in 0.5% CMC—Na solution was administered orally to the animals in a forced manner. The animals were observed for emesis occurred within 3 hours after the test compound administration. Next, each maximum tolerance dose against emesis was obtained. The results are shown in Table 3. Rolipram as described in Assay Example 1 was used for the reference compound in this assay.

TABLE 3

| Test Compounds | (mg/kg) Maximum Tolerance Dose against Emesis |
|---|---|
| Example No. 8 | 0.3 |
| Example No. 10 | >3 |
| Rolipram | <0.1 |

Conclusion

As seen in Table 3, it has been ascertained that, for the compounds of the present invention, their maximum tolerance dose levels against emesis are higher than that of rolipram. Thus, the compounds of the present invention are apparently less emetic as compared with rolipram.

Assay Example 5

Inhibition of TNF-α Production in Lipopolysaccharide (LPS)-Stimulated Macrophages In order to measure inhibitory activity on LPS-induced TNFα production in mouse peritoneal macrophages according to Eur. J. Pharmacol., 230, 9-14 (1993), the following assay was employed.

1) Preparation of Mouse Peritoneal Macrophages

Ten percent proteose peptone (2 ml/animal) was administered intraperitoneally to male C3H/HeN mice (6- to 8-week-old) for inducing peritoneal macrophages. Four days after the proteose peptone administration, mice were sacrificed by the dislocation of cervical vertebrate, bled with cutting of their carotid artery, douched intraperitoneally with ice-cooled RPMI 1640 (6 ml), massaged, and lavage fluids wherein peritoneal exudate cells suspended were harvested. The resulting cell suspension was centrifuged at 200×g, and obtained cell pellets were treated with a Tris-ammonium buffer for 1 minute to hemolyze erythrocyte contaminants. The resulting cells were washed twice with 10% FBS/RPMI 1640, resuspended, and seeded on 96-well plates (Sumitomo Bakelite, Japan) at $5 \times 10^5$ cells/0.2 ml/well. After pre-incubation for 2 hours in an atmosphere of 5% $CO_2$/95% air, each well was rinsed 3 times with PBS(-) to remove non-adhesive cells.

2) Cell Treatment

Each test compound was dissolved in DMSO, and then in 10% FBS/RPMI 1640 to make the final DMSO concentration 0.1%. The resultant test compound solution was used herein. After pre-incubation for 0.5 hr in the above test compound solution, an aliquot of macrophages prepared in the above (1) was admixed with LPS (*E. coli* serotype 0127: B8; Sigma) to adjust the final LPS concentration to 0.1 μg/ml. Four hours later, culture supernatants were harvested and stored at -80° C. Amounts of TNFα in the culture supernatants were measured with a mouse TNFα ELISA kit (Quantikine/trade name; R & D Systems) according to manuals attached to the kit. For control groups, an aliquot of macrophages prepared in the above (1) was admixed with LPS to adjust the final LPS concentration to 0.1 μg/ml and then treated in the same manner as aforementioned. The resultant samples were used in obtaining the concentration of each test compound required for 50% inhibition ($IC_{50}$) to each control group.

When the above assay was applied to Example No. 8 Compound and rolipram, their excellent inhibitory activity on the production of TNF-α were observed. The $IC_{50}$ value for Example No. 8 Compound is 0.34 g/ml (about 0.88 μg M) and that for rolipram 0.37 μg/ml (about 1.3 μM).

When the above assay was conducted for Compounds A, B and D in Table 1 of JP, A, 63-159382 (1988), the percent inhibition of TNF-α production to the control group is 12%, 22% and 6% for Compounds A, B and D at 0.1 μM; 26%, 40% and 31% at 1.0 μM; and 39%, 36% and 40% at 10 μM, respectively. Accordingly, all the $IC_{50}$ values thereof are apparently higher than 10 μM.

From these results, it has been ascertained that the compounds of the present invention are excellently active on the inhibition of TNF-α production as compared with the prior art compounds as disclosed in JP, A, 63-159382 (1988).

Synthetic Examples

Described below are Synthetic Examples 1 to 3 for the compounds of the formula (2) and Synthetic Examples 4 to 19 for the compounds of the formula (3). Besides, Synthetic Example 20 for the compound of the formula (2) and Synthetic Examples 21 to 24 for the compounds of the formula (3) are also disclosed herein.

Synthetic Example 1

6-Methyl-2-(3-nitrophenylamino)nicotinaldehyde (1) A mixture of 2-chloro-6-methylnicotinic acid (10 g, 58.28 mmol), 3-nitroaniline (16.10 g, 116.66 mmol), potassium carbonate (9.26 g, 67.20 mmol) and copper oxide (232 mg, 2.91 mmol) was allowed to stand at 150° C. for 4 hours. After admixing with water, the mixture was allowed to cool, and filtered to remove an insoluble. To the filtrate was added conc. hydrochloric acid. The resultant precipitate was filtered to give a product as a crystal. The product was washed successively with hydrochloric acid and water, and dried to give 6-methyl-2-(3-nitrophenylamino)nicotinic acid (15.06 g, 95%).

$^1$H NMR(CDCl$_3$) δ: 2.58(3H,s), 6.74–6.77(1H, app-d, J=5.9 Hz), 7.44–7.50(1H, app-t, J=8.2 Hz), 7.86–7.99(2H, m), 8.23–8.26(1H, app-d, J=7.9 Hz), 8.95–8.96(1H, app-t, J=2.0 Hz), 10.33(1H, brs).

(2) To a suspension of 6-methyl-2-(3-nitrophenylamino)-nicotinic acid (15.06 g, 55.11 mmol) in acetone (220ml) was added triethylamine (6.13 g, 60.6 mmol) and chloroacetonitrile (4.58 g, 60.6 mmol), and the mixture was heated under reflux overnight. The reaction mixture was filtered to remove an insoluble. The filtrate was evaporated. The resultant residue was washed successively with 1N aqueous sodium hydroxide and water, and dried to give 6-methyl-2-(3-nitrophenylamino)nicotinic acid cyanomethyl ester (15.44 g, 90%).

$^1$H NMR(CDCl$_3$) δ: 2.58(3H,s), 4.98(2H, s), 6.73–6.76 (1H, app-d, J=8.2 Hz), 7.44–7.50(1H, app-t, J=8.2 Hz), 7.88–7.92(2H, m), 8.15–8.18(1H, app-d, J=8.2 Hz), 8.98–8.99(1H, app-t, J=2.0 Hz), 10.16(1H, brs).

(3) A mixture of 6-methyl-2-(3-nitrophenylamino) nicotinic acid cyanomethyl ester (15.44 g, 49.43 mmol) and triethylamine (1.00 g, 9.89 mmol) in dry methanol (160 ml) was heated under reflux overnight. After cooling, crystals were collected by filtration, washed with methanol, and dried to give 6-methyl-2-(3-nitrophenylamino)nicotinic acid methyl ester (13.84 g, 97%).

$^1$H NMR(CDCl$_3$) δ: 2.56(3H,s), 3.94(3H, s), 6.69–6.72 (1H, app-d, J=8.2 Hz), 7.41–7.47(1H, app-t, J=8.2 Hz), 7.83–7.95(2H, m), 8.15–8.18(1H, app-d, J=7.9 Hz), 9.00–9.02(1H, app-t, J=2.0 Hz), 10.53(1H, brs).

(4) To a solution of 6-methyl-2-(3-nitrophenylamino) nicotinic acid methyl ester (13.84 g, 48.18 mmol) in THF (180 ml) was added potassium borohydride (3.12 g, 57.82 mmol) and lithium chloride (2.45 g, 58.82 mmol) and the mixture was heated under reflux. Potassium borohydride (0.52 g, 9.64 mmol) was added three times at one hour intervals and the mixture was further heated under reflux for 1 hour. Evaporation of the solvent under reduced pressure gave a residue which was admixed with water to form crystals. The crystals were collected by filtration, washed successively with water and isopropanol, and dried to give 3-hydroxymethyl-6-methyl-2-(3-nitrophenylamino)-pyridine (11.05 g, 88%).

$^1$H NMR(DMSO-$d_6$) δ: 2.40(3H,s), 4.58(2H, d, J=5.3 Hz), 5.46(1H, t, J=5.3 Hz), 6.76–6.79(1H, app-d, J=7.3 Hz), 7.49–7.55(1H, app-t, J=8.2 Hz), 7.54–7.56(1H, app-d, J=7.6 Hz), 7.70–7.73(1H, app-dd, J=1.3 Hz, 8.2 Hz), 8.06–8.09 (1H, app-dd, J=1.3 Hz, 8.2 Hz), 8.46(1H, s), 8.85–8.86(1H, app-t, J=2.0 Hz).

(5) To a suspension of 3-hydroxymethyl-6-methyl-2-(3-nitrophenylamino)pyridine (11.05 g, 42.62 mmol) in chloroform (200 ml) was added manganese dioxide (50 g), and the mixture was stirred overnight and filtered to remove an insoluble. Evaporation of the solvent from the filtrate gave a residue. Recrystallization of the resultant residue from acetonitrile gave 6-methyl-2-(3-nitrophenylamino) nicotinaldehyde (7.90 g, 72%).

$^1$H NMR(CDCl$_3$) δ: 2.60(3H,s), 6.82–6.85(1H, app-d, J=7.9 Hz), 7.45–7.51(1H, app-t, J=8.2 Hz), 7.81–7.84(1H, app-d, J=7.6 Hz), 7.88–7.98(2H, m), 9.06–9.08(1H, app-t, J=2.0 Hz), 9.86(1H, s), 10.76(1H, brs).

Synthetic Example 2

6-Methyl-2-(3-methylthiophenylamino) nicotinaldehyde

The procedure of Synthetic Example 1 was repeated using 2-chloro-6-methylnicotinic acid and 3-methylthioaniline to obtain 6-methyl-2-(3-methylthiophenylamino) nicotinaldehyde.

$_1$H NMR(CDCl$_3$) δ: 2.52(6H, s), 6.69–6.72(1H, app-d, J=7.6 Hz), 6.94–6.98(1H, m), 7.20–7.26(1H, app-t, J=7.9 Hz), 7.47–7.51(1H, m), 7.72–7.45(1H, app-d, J=7.6 Hz), 7.94–7.95(1H, app-t, J=2.0 Hz), 9.79(1H, s), 10.52(1H, brs).

Synthetic Example 3

2-(Pyridin-3-ylamino)nicotinaldehyde

The procedure of Synthetic Example 1 or partly modified processes thereof were repeated using 2-chloronicotinic acid and 3-aminopyridine to obtain 2-(pyridin-3-ylamino) nicotinaldehyde.

$^1$H NMR(CDCl$_3$) δ: 6.91–6.95(1H, app-dd, J=4.7 Hz, 7.5 Hz), 7.27–7.32(1H, m), 7.91–7.95(1H, app-dd, J=1.9 Hz, 7.5 Hz), 8.29–8.34(2H, m), 8.43–8.46(1H, app-dd, J=1.9 Hz, 4.9 Hz), 8.87–8.88(1H, m), 9.91(1H, s), 10.47(1H, brs).

Synthetic Example 4

Ethyl 3-(pyridin-2-yl)propionate (1) To a suspension of sodium hydride (60% in oil, 0.88 g, 22 mmol) in THF (20 ml) was added ethyl diethylphosphonoacetate (4.93 g, 22 mmol) dropwise while ice cooling and the mixture was further stirred at room temperature for 15 minutes and again ice cooled. To the ice cooled mixture was added dropwise a solution of picolinaldehyde (2.14 g, 20 mmol) in THF (10 ml). After the addition, the reaction mixture was heated at 60° C. for 1 hour. Thereafter, the reaction was stopped by treating with 1M aqueous acetic acid. The mixture was diluted with water, and extracted with methylene chloride. The organic layer was treated according to conventional techniques. Evaporation of the solvent yielded a residue which was subjected to recrystallization from hexane to afford ethyl 3-(pyridin-2-yl)-acrylate, yield: 80%.

$^1$H NMR(CDCl$_3$) δ: 1.34(3H, t, J=7.26 Hz), 4.28(2H, q, J=7.26 Hz), 6.92(1H, d, J=15.84 Hz), 7.24–7.29(1H, m), 7.42–7.45(2H, app-d, J=7.59 Hz), 7.69(1H, d, J=15.84 Hz), 7.66–7.75(1H, m), 8.64–8.66 (1H, app-d, J=4.62 Hz).

(2) To a suspension of ethyl 3-(pyridin-2-yl)acrylate (2.8 g) in methanol (150 ml) was added 10% palladium on carbon (230 mg) and the mixture was stirred under hydrogen gas atmosphere for 3 hours at room temperature and then filtered to remove an insoluble. Evaporation of solvent from the filtrate yielded ethyl 3-(pyridin-2-yl)propionate (2.5 g, 88%).

$^1$H NMR(CDCl$_3$) δ: 1.23(3H, t, J=7.26 Hz), 2.80(2H, t, J=7.59 Hz), 3.12(2H, t, J=7.59 Hz), 4.15(2H, q, J=7.26 Hz), 7.09–7.20(2H, m), 7.56–7.62(1H, app-dt, J=1.65 Hz, 7.59 Hz), 8.52–8.53(1H, m).

Synthetic Example 5

Ethyl 3-(pyridin-3-yl)propionate

The procedure of Synthetic Example 4 was repeated using nicotinaldehyde and ethyl diethylphosphonoacetate to obtain ethyl 3-(pyridin-3-yl)propionate.

$^1$H NMR(CDCl$_3$) δ: 1.23(3H, t, J=6.93 Hz), 2.64(2H, t, J=7.58 Hz), 2.96(2H, t, J=7.58 Hz), 4.13(2H, q, J=6.93 Hz), 7.19–7.24(1H, m), 7.52–7.56(1H, m), 8.45–8.49(2H, m).

Synthetic Example 6

Ethyl 3-(pyridin-4-yl)propionate

The procedure of Synthetic Example 4 was repeated using isonicotinaldehyde and ethyl diethylphosphonoacetate to obtain ethyl 3-(pyridin-4-yl)propionate.

$^1$H NMR (CDCl$_3$) δ: 1.24 (3H, t, J=7.2 Hz), 2.65 (2H, t, J=7.6 Hz), 2.95 (2H, t, J=7.6 Hz), 4.14 (2H, q, J=7.2 Hz), 7.12–7.15 (2H, m), 8.49–8.52 (2H, m).

Synthetic Example 7

Methyl 4-(pyridin-3-yl)butanoate (1) A mixture of 3-bromopyridine (3.7 ml, 38.0 mmol), 3-butenoic acid (3.2 ml, 38.0 mmol), palladium acetate (85 mg, 1 mol %) and tri-o-tolylphosphine (231 mg, 2 mol %) in DMF (12 ml) was stirred at 100° C. overnight under nitrogen atmosphere. Triethylamine (3.84 g, 38.0 mmol) was then added to the mixture which was further stirred overnight, filtered to remove an insoluble, and washed with DMF. Evaporation of solvent from the filtrate yielded a residue. A mixture of the resultant residue and palladium on activated carbon (300 mg) in methanol (50 ml) was stirred under hydrogen atmosphere. After completion of the reduction, the reaction mixture was filtered. Evaporation of solvent from the filtrate yielded a residue. To the resulting residue (5.40 g, an equivalent to 32.6 mmol) was added sodium hydrogen carbonate (2.74 g, 32.6 mmol) and water, and the mixture was stirred followed by removal of water on an evaporator. To the residue was added acetone (80 ml) and chloroacetonitrile (2.47 g, 32.7 mmol), and the mixture was heated under reflux overnight.

After filtration of the reaction mixture, the filtrate was evaporated. The resultant residue was subjected to purification using column chromatography on silica gel to afford a target product, cyanomethyl 4-(pyridin-3-yl)butanoate (0.57 g, 7.4%).

$^1$H NMR(CDCl$_3$) δ: 2.01(2H, app-qw, J=7.3 Hz, 7.3 Hz), 2.45(2H, t, J=7.3 Hz), 2.69(2H, t, J=7.3 Hz), 4.72(2H, s), 7.22–7.27(1H, m), 7.49–7.54(1H, m), 8.45–8.49(2H, m).

(2) A mixture of cyanomethyl 4-(pyridin-3-yl)butanoate (0.57 g, 2.81 mmol) and triethylamine (57 mg, 0.56 mmol) in dry methanol (10 ml) was heated under reflux overnight, and evaporated to give a residue. The resultant residue was subjected to purification using column chromatography on silica gel to afford a target product, methyl 4-(pyridin-3-yl)butanoate (0.46 g, 92%).

$^1$H NMR(CDCl$_3$) δ: 1.97(2H, app-qw, J=7.3 Hz, 7.3 Hz), 2.35(2H, t, J=7.3 Hz), 2.66(2H, t, J=7.3 Hz), 3.68(2H, s), 7.20–7.25(1H, m), 7.49–7.53(1H, m), 8.41–8.48(2H, m).

Synthetic Example 8

Methyl 4-(pyridin-4-yl)butanoate (1) To a solution of diethyl malonate (9.6 g, 0.06mol) in 20 ml of absolute ethanol was added sodium ethoxide (4.1 g) portionwise at room temperature while stirring and the mixture was further stirred for 4 hours followed by dropwise addition of 4-vinylpyridine (2.1 g, 0.02 mol). The mixture was then stirred overnight. Evaporation of ethanol under reduced pressure gave a residue to which was added water followed by neutralization with 3N hydrochloric acid. The mixture was extracted with ethyl acetate. The extracted liquid was treated according to conventional techniques. Evaporation of solvent yielded a residue which was subjected to purification using column chromatography on silica gel to afford diethyl 2-(pyridin-4-yl)ethylmalonate as an oil (2.46 g, 46%).

$^1$H NMR(CDCl$_3$) δ: 1.28(6H, t, J=7.2 Hz), 2.19–2.27(2H, m), 2.67(2H, t, J=7.2 Hz), 3.33(1H, t, J=7.2 Hz), 4.22(4H, q, J=7.2 Hz), 7.13(2H, d, J=6.0 Hz), 8.51(2H, d, J=6.0 Hz).

(2) A mixture of diethyl 2-(pyridin-4-yl)ethylmalonate (2.4 g, 0.009 mol) and 30 ml of conc. hydrochloric acid was heated at 100° C. for 15 hours and an excess amount of hydrochloric acid was then evaporated under reduced pressure. A mixture of the resultant residue and 10% hydrochloric acid-methanol solution was heated under reflux, evaporated, neutralized with saturated aqueous sodium hydrogen carbonate, and extracted with ethyl acetate. The extract was treated according to conventional techniques. Evaporation of solvent yielded the title compound, methyl 4-(pyridin-4-yl)butanoate, as an oil (0.62 g, 39%).

$^1$H NMR(CDCl$_3$) δ: 1.92–2.03(2H, m), 2.35(2H, t, J=7.4 Hz), 2.66(2H, t, J=7.4 Hz), 3.68(3H, s), 7.12(2H, d, J=6.0 Hz), 8.51(2H, d, J=6.0 Hz).

Synthetic Example 9

Ethyl 5-(pyridin-3-yl)pentanoate

A solution of LDA (16.5 ml of 2M solution, 3.5 g, 0.03 mol) in THF (100 ml) was cooled to −70° C. or below (dry ice-methanol bath) under a nitrogen flow and treated dropwise with ethyl 4-diethylphosphonocrotonate (8.6 g, 0.037 mmol) while stirring. The mixture was further stirred for 15 minutes, treated dropwise with nicotinaldehyde (3.2 g, 0.030 mol), and then stirred at 0° C. for 1.5 hours. Next, the mixture was treated with acetic acid and evaporated. To the residue was added saturated aqueous sodium hydrogen carbonate and the mixture was extracted with ethyl acetate. The extract was treated according to conventional techniques. Evaporation of solvent yielded ethyl 5-(pyridin-3-yl)penta-2,4-dienoate as an oil (6.7 g).

This compound was dissolved in 50 ml of ethanol without purification. To the solution was added 200 mg of 10% palladium on carbon and the mixture was stirred for 19 hours under a hydrogen flow. After the catalyst was filtered off, the filtrate was evaporated to give the title compound, ethyl 5-(pyridin-3-yl)pentanoate, as an oil (4.8 g, 78%).

$^1$H NMR(CDCl$_3$) δ: 1.25(3H, t, J=7.1 Hz), 1.64–1.70(4H, m), 2.33(2H, t, J=6.9 Hz), 2.63(2H, t, J=6.9 Hz), 4.12(2H, q, J=7.1 Hz), 7.18–7.23(1H, m), 7.48(1H, d, J=7.9 Hz), 8.42–8.45 (2H, m).

Synthetic Example 10

Ethyl 5-(pyridin-4-yl)pentanoate

The procedure of Synthetic Example 9 was repeated using isonicotinaldehyde as the starting material in place of nicotinaldehyde to obtain ethyl 5-(pyridin-4-yl)pentanoate.

$^1$H NMR(CDCl$_3$) δ: 1.25(3H, t, J=7.1 Hz), 1.64–1.70(4H, m), 2.33(2H, t, J=6.9 Hz), 2.62(2H, bs), 4.12(2H, q, J=7.1 Hz), 7.10(2H, d, J=6.0 Hz), 8.48 (2H, d, J=6.0 Hz).

Synthetic Example 11

Methyl 6-(pyridin-2-yl)hexanoate (1) A mixture of 5-bromopentanoic acid (6.9 g, 38 mmol) and triphenylphosphine (10 g, 38 mmol) in dry acetonitrile (30 ml) was heated under reflux overnight. Evaporation of solvent yielded crystals. The resultant crystals were washed with a small amount of acetonitrile and dried at room temperature under reduced pressure to afford a target product, (4-carboxybutyl)-triphenylphosphonium bromide (14.6 g, 87%), which was used in the next step without any further treatment.

(2) To sodium hydride (oily dispersion, 2.31 g, 57.8 mmol) was added dry DMSO (30 ml) and the mixture was stirred at 60° C. for 2 hours. The NaH-DMSO reaction product was added dropwise to a mixture of (4-carboxybutyl)triphenylphosphonium bromide (12.77 g, 28 mmol) and dry DMSO (5 ml) at room temperature. Thirty minutes later, the mixture was treated dropwise with picolinaldehyde (2.3 ml, 24 mmol) and stirred overnight. Solvent was distilled off under reduced pressure. To the residue was added water, and the mixture was washed twice with benzene and evaporated under reduced pressure to remove water.

To the residue was added acetone (60 ml) and chloroacetonitrile (2.72 g, 36 mmol) and the mixture was heated under reflux for 1 hour and treated with water. Acetone was evaporated under reduced pressure and the resultant residue was extracted with ethyl acetate. The extract was treated according to conventional techniques and then evaporated to remove the solvent. The residue was subjected to purification using column chromatography on silica gel to afford a target product, 6-(pyridin-2-yl)-5-hexenoic acid cyanomethyl ester (4.83 g, 87%).

Cis isomer, $^1$H NMR(CDCl$_3$) δ: 1.86(2H, tt, J=7.6, 7.6 Hz), 2.47 (2H, t, J=7.6 Hz), 2.68–7.67(2H, dt, J=7.6, 7.6 Hz), 4.68(2H, s), 5.82(1H, dt, J=7.6, 11.9 Hz), 6.49(1H, dt, J=1.7, 11.6 Hz), 7.09–7.13(1H, m), 7.18–7.21(1H, app-d, J=7.9 Hz), 7.61–7.67(1H, app-dt, J=1.7, 7.6 Hz), 8.57–8.60 (1H, m).

Trans isomer, $^1$H NMR(CDCl$_3$) δ: 1.90(2H, tt, J=7.6, 7.6 Hz), 2.30–2.38(2H, dt, J=6.6, 6.9 Hz), 2.49(2H, t, J=7.3 Hz), 4.71(2H, s), 6.50(1H, d, J=15.8 Hz), 6.69(1H, dt, J=6.9, 15.8 Hz), 7.09–7.14(1H, m), 7.22–7.25(1H, app-d, J=7.9 Hz), 7.59–7.65(1H, app-dt, J=2.0, 7.6 Hz), 8.52–8.54(1H, m).

(3) To 6-(pyridin-2-yl)-5-hexenoic acid cyanomethyl ester (4.83 g, 21.0 mmol) was added methanol (50 ml) and triethylamine (0.405 g, 4.0 mmol) and the mixture was heated under reflux overnight and then evaporated to remove the solvent. The resultant residue was subjected to purification using column chromatography on silica gel to afford a target product, methyl 6-(pyridin-2-yl)-5-hexenoate (4.97 g, quantitative).

Cis isomer, $^1$H NMR(CDCl$_3$) δ: 1.82(2H, tt, J=7.6, 7.6 Hz), 2.37 (2H, t, J=7.6 Hz), 2.62–7.71(2H, dt, J=7.6, 7.6 Hz), 3.64(3H, s), 5.85(1H, dt, J=7.3, 11.9 Hz), 6.48(1H, dt, J=1.7, 11.9 Hz), 7.07–7.12(1H, m), 7.20–7.22(1H, app-d, J=7.9 Hz), 7.60–7.66(1H, app-dt, J=1.7, 7.6 Hz), 8.57–8.60 (1H, m).

Trans isomer, $^1$H NMR(CDCl$_3$) δ: 1.86(2H, tt, J=7.3, 7.3 Hz), 2.28–2.42(4H, m), 3.67(3H, s), 6.50(1H, d, J=15.5 Hz), 6.68(1H, dt, J=6.9, 15.5 Hz), 7.09–7.14(1H, m), 7.26–7.29 (1H, app-d, J=7.9 Hz), 7.59–7.66(1H, app-dt, J=1.7, 7.6 Hz), 8.50–8.53(1H, m).

(4) A mixture of methyl 6-(pyridin-2-yl)-5-hexenoate (4.97 g, 21.0 mmol) and 10% palladium on carbon (200 mg) in methanol (100 ml) was stirred overnight under hydrogen atmosphere. The reaction mixture was filtered. Evaporation of solvent from the filtrate yielded a target product, methyl 6-(pyridin-2-yl)-hexanoate (4.1 g, 94%).

$^1$H NMR(CDCl$_3$) δ: 1.33–1.45(2H, m), 1.62–1.80(4H, m), 2.32(2H, t, J=7.3 Hz), 2.79(2H, t, J=7.6 Hz), 3.66(3H, s), 7.10–7.17(2H, m), 7.58–7.64(1H, app-dt, J=2.0, 7.6 Hz), 8.49–8.52(1H, m).

Synthetic Example 12

Methyl 6-(pyridin-3-yl)hexanoate

The steps (2) to (4) of Synthetic Example 11 were repeated using (4-carboxybutyl)triphenylphosphonium bromide and nicotinaldehyde to obtain methyl 6-(pyridin-3-yl) hexanoate.

$^1$H NMR(CDCl$_3$) δ: 1.31–1.43(2H, m), 1.59–1.72 (4H, m), 2.31 (2H, t, J=7.6 Hz), 2.62(2H, t, J=7.3 Hz), 3.66(3H, s), 7.19–7.23 (1H, app-dd, J=5.0, 7.9 Hz), 7.47–7.51(1H, app-dt, J=1.7, 7.9 Hz), 8.42–8.44(2H, m).

Synthetic Example 13

Methyl 6-(pyridin-4-yl)hexanoate

The steps (2) to (4) of Synthetic Example 11 were repeated using (4-carboxybutyl)triphenylphosphonium bromide and isonicotinaldehyde to obtain methyl 6-(4-pyridyl) hexanoate.

$^1$H NMR(CDCl$_3$) δ: 1.31–1.42(2H, m), 1.60–1.72(4H, m), 2.31 (2H, t, J=7.26 Hz), 2.61(2H, t, J=7.59 Hz), 3.66(3H, s), 7.09–7.11(2H, app-d, J=5.94 Hz), 8.47–8.49(2H, app-dd, J=6.27 Hz).

Synthetic Example 14

Methyl 7-(pyridin-3-yl)heptanoate

The procedure of Synthetic Example 11 was repeated using 6-bromohexanoic acid to methyl 7-(pyridin-3-yl) heptanoate.

$^1$H NMR(CDCl$_3$) δ: 1.28–1.42(4H, m), 1.56–1.68(4H, m), 2.30(2H, t, J=7.3 Hz), 2.61(2H, t, J=7.3 Hz), 3.67(3H, s), 7.19–7.24(1H, m), 7.48–7.52(1H, app-dt, J=2.3, 7.6 Hz), 8.41–8.43(2H, m).

Synthetic Example 15

Methyl 7-(pyridin-4-yl)heptanoate

The steps (2) to (4) of Synthetic Example 11 were repeated using (5-carboxypentyl)triphenylphosphonium bromide which was obtained as an intermediate in Synthetic Example 14 and isonicotinaldehyde to methyl 7-(pyridin-4-yl)heptanoate.

$^1$H NMR(CDCl$_3$) δ: 1.32–1.38(4H, m), 1.50–1.70(4H, m), 2.30 (2H, t, J=7.6 Hz), 2.63(2H, t, J=7.6 Hz), 3.66(3H, s), 7.09–7.11(2H, app-d, J=5.9 Hz), 8.47–8.49(2H, app-d, J=6.3 Hz).

Synthetic Example 16

Methyl 9-(pyridin-4-yl)nonanoate

The procedure of Synthetic Example 11 was repeated using 8-bromooctanoic acid to methyl 9-(pyridin-4-yl) nonanoate.

$^1$H NMR(CDCl$_3$) δ: 1.30(8H, m), 1.57-1.67(4H, m), 2.30(2H, t, J=7.6 Hz), 2.59(2H, t, J=7.6 Hz), 3.67(3H, s), 7.09–7.11(2H, app-d, J=5.9 Hz), 8.47–8.49(2H, app-d, J=5.9 Hz).

Synthetic Example 17

Ethyl 4-(2-thienyl)butanoate

A mixture of 4-(2-thienyl)butanoic acid (2.50 g, 14.7 mmol) and hydrochloric acid-methanol (50 ml) was stirred overnight at room temperature. Solvent was distilled off and the residue was dissolved in ethyl acetate, washed with water, dried over anhydrous magnesium sulfate, and evaporated. The resultant residue was subjected to purification using column chromatography on silica gel to afford ethyl 4-(2-thienyl)butanoate (2.41 g, 89%).

$^1$H NMR(CDCl$_3$) δ: 2.02(2H, tt, J=7.3 Hz, 7.3 Hz), 2.38(2H, t, J=7.3 Hz), 2.88(2H, t, J=7.3 Hz), 3.67(3H, s), 6.78–6.81(1H, m), 6.90–6.93(1H, app-dd, J=3.6 Hz, 5.3 Hz), 7.11–7.14(1H, m).

Synthetic Example 18

Ethyl 5-(2-furyl)pentanoate

To a mixture of LDA (2M solution) (11.5 ml, 22.9 mmol) and THF (60 ml) was added dropwise triethyl 4-phosphonocrotonate (5.73 g, 22.9 mmol) while cooling with a dry ice-methanol bath. Fifteen minutes later, the mixture was treated dropwise with furfural (2.00 g, 20.8 mmol), and stirred for 1 hour in an ice bath and further at room temperature overnight. The resultant mixture was diluted with ethyl acetate, washed successively with dilute hydrochloric acid (1N, twice), saturated aqueous sodium chloride, saturated aqueous carbonic acid (twice) and saturated aqueous sodium chloride, dried over anhydrous magnesium sulfate, and evaporated.

To the resultant residue was added ethanol (60 ml) and palladium/activated carbon (150 mg) and the mixture was stirred under hydrogen atmosphere, filtered, and evaporated. The resultant residue was subjected to purification using column chromatography on silica gel to afford ethyl 5-(2-furyl)pentanoate (1.82 g, 45%).

$^1$H NMR(CDCl$_3$) δ: 1.25(3H, t, J=7.3 Hz), 1.60–1.75(4H, m), 2.78–2.37(2H, m), 2.61–2.69(2H, m), 4.13(2H, q, J=7.3 Hz), 5.98–6.00(1H, m), 6.26–6.28(1H, app-dd, J=1.6 Hz, 3.0 Hz), 7.29–7.30(1H, m).

Synthetic Example 19

Ethyl 5-(3-furyl)pentanoate

The procedure of Synthetic Example 18 was repeated using 3-furaldehyde to ethyl 5-(3-furyl)pentanoate.

$^1$H NMR(CDCl$_3$) δ: 1.25(3H, t, J=7.3 Hz), 1.53–1.73(4H, m), 2.32(2H, t, J=7.3 Hz), 2.44(2H, t, J=7.3 Hz), 4.13(2H, q, J=7.3 Hz), 6.25–6.26(1H, app-t, J=1.0 Hz), 7.20–7.22(1H, m), 7.34–7.35(1H, app-t, J=1.7 Hz).

Synthetic Example 20

2-(3-Methylsulfonylphenylamino)nicotinaldehyde (1) The steps (1) and (2) of Synthetic Example 1 were repeated using 2-chloronicotinic acid and 3-methylthioaniline to obtain cyanomethyl 2-(3-methylthiophenylamino)nicotinate (1.88 g, 6.28 mmol). The product was dissolved in chloroform (65 ml), and treated dropwise with a solution of m-chloroperbenzoic acid (purity 70%, 3.10 g, 2.0 eq.) in chloroform (50 ml) while ice cooling. The mixture was stirred for 1 hour, and washed with saturated aqueous sodium hydrogen carbonate. The organic layer was dried over anhydrous magnesium sulfate, and evaporated to give cyanomethyl 2-(3-methylsulfonylphenylamino)nicotinate (2.08 g, quantitative).

$^1$H NMR(CDCl$_3$) δ: 3.10(3H,s), 5.00(2H, s), 6.85–6.89 (1H, app-dd, J=4.6 Hz, 7.9 Hz), 7.51–7.56(1H, app-t, J=7.9 Hz), 7.61–7.65(1H, app-dt, J=1.3 Hz, 7.9 Hz), 7.94–7.98 (1H, app-ddd, J=1.0 Hz, 2.3 Hz, 7.9 Hz), 8.27–8.31(1H, app-dd, J=2.0 Hz, 7.9 Hz), 8.43–8.45(1H, app-t, J=2.0 Hz), 8.48–8.51(1H, app-dd, J=2.0 Hz, 4.6 Hz), 10.12 (1H, brs).

(2) The steps (3), (4) and (5) of Synthetic Example 1 were repeated using cyanomethyl 2-(3-methylsulfonylphenylamino)-nicotinate to obtain 2-(3-methylsulfonylphenylamino)-nicotinaldehyde.

$^1$H NMR(CDCl$_3$) δ: 3.10(3H,s), 6.94–6.99(1H, app-dd, J=4.9 Hz, 7.6 Hz), 7.51–7.57(1H, app-t, J=7.9 Hz), 7.62–7.66(1H, app-dt, J=1.3 Hz, 7.9 Hz), 7.93–7.97(1H, app-dd, J=2.0 Hz, 7.6 Hz), 7.98–8.02(1H, app-ddd, J=1.0 Hz, 2.0 Hz, 7.9 Hz), 8.47–8.49(1H, app-dd, J=2.0 Hz, 4.6 Hz), 8.53–8.55(1H, app-t, J=2.0 Hz), 9.92(1H, s), 10.68(1H, brs).

Synthetic Example 21

Ethyl 5-(2-pyridyl)pentanoate

The procedure of Synthetic Example 9 was repeated using picolinaldehyde in place of nicotinaldehyde to ethyl 5-(2-pyridyl)pentanoate.

$^1$H NMR(CDCl$_3$) δ: 1.25(3H, t, J=7.3 Hz), 1.63–1.84(2H, m), 2.34(2H, t, J=7.5 Hz), 2.81(2H, t, J=7.5 Hz), 4.12(2H, q, J=7.3 Hz), 7.07–7.16(2H, m), 7.56–7.62(1H, app-dt, J=2.0 Hz, 7.6 Hz), 8.51–8.53(1H, m).

Synthetic Example 22

Methyl 4-(2-benzothiazolyl)butanoate

A solution of 4-(2-benzothiazolyl)butanoic acid (3.75 g, 16.1 mmol, prepared according to the procedure of Example 11 in JP, A, 8-208631 (1996)) in hydrochloric acid-methanol (80 ml) was stirred at room temperature overnight, and evaporated. The residue was dissolved in chloroform, and washed with saturated aqueous sodium hydrogen carbonate. The organic layer was dried over anhydrous magnesium sulfate, evaporated, and purified through flash column chromatography to give methyl 4-(2-benzothiazolyl)butanoate (2.75 g, 73%).

$^1$H NMR(CDCl$_3$) δ: 2.23(2H, tt, J=7.3 Hz, 7.6 Hz), 3.49(2H, t, J=7.6 Hz), 3.18(2H, t, J=7.3 Hz), 3.68(3H, s), 7.33–7.39(1H, app-t, J=7.3 Hz), 7.43–7.49(1H, app-t, J=7.3 Hz), 7.83–7.86(1H, app-d, J=7.9 Hz), 7.96–7.99(1H, app-d, J=7.9 Hz).

Synthetic Example 23

Methyl 5-(2-benzothiazolyl)pentanoate

A solution of 5-(2-benzothiazolyl)pentanoic acid (1.54 g, 6.5 mmol, prepared according to the procedure of Example 12 in JP, A, 8-208631 (1996)) in hydrochloric acid-methanol (40 ml) was stirred at room temperature overnight, and evaporated. The residue was dissolved in chloroform, and washed with saturated aqueous sodium hydrogen carbonate. The organic layer was dried over anhydrous magnesium sulfate, evaporated, and purified through flash column chromatography to give methyl 5-(2-benzothiazolyl)pentanoate (1.08 g, 67%).

$^1$H NMR(CDCl$_3$) δ: 1.73–1.84(2H, m), 1.88–2.00(2H, m), 3.39(2H, t, J=7.3 Hz), 3.14(2H, t, J=6.9 Hz), 3.67(3H, s), 7.32–7.38(1H, app-t, 7.9 Hz), 7.43–7.48(1H, app-t, 7.9 Hz), 7.83–7.86(1H, app-d, J=7.9 Hz), 7.95–8.98(1H, app-d, J=8.2 Hz).

Synthetic Example 24

Ethyl 5-(2-thiazolyl)pentanoate

The procedure of Synthetic Example 9 or partly modified processes thereof were repeated using thiazole-2-aldehyde in place of nicotinaldehyde to obtain ethyl 5-(2-thiazolyl) pentanoate.

$^1$H NMR(CDCl$_3$) δ: 1.25(3H, t, J=7.3 Hz), 1.68–1.92 (4H, m), 2.35(2H, t, J=7.6 Hz), 3.06(2H, t, J=7.9 Hz), 4.13(3H, q, J=7.3 Hz), 7.19–7.20(1H, app-d, J=3.3 Hz), 7.67–7.68(1H, app-d, J=3.3 Hz).

Example 1

1-(3-Nitrophenyl)-3-(pyridin-2-ylmethyl)-1,8-naphthyridin-2(1H)-one

Ethyl 3-(pyridin-2-yl)propionate (0.717 g, 2.0 eq., prepared in Synthetic Example 4) was dissolved in dry THF. To the solution was added LDA (2 ml of 2M solution, 2.0 eq.) at −78° C. or below in a methanol-dry ice bath under nitrogen atmosphere while stirring and the mixture was stirred for 1 hour. Next, to the reaction mixture was added dropwise a solution of 2-(3-nitrophenylamino) nicotinaldehyde (486 mg, 1.0 eq., prepared according to the procedure of Example 3 in JP, A, 62-228076 (1987)) in THF and the resultant mixture was stirred for 2 hours at −78° C. and then continued to stir for 24 hours until it reached room temperature. The reaction mixture was treated with water, and extracted with methylene chloride. The organic layer was dried, and evaporated. To the residue was added ethyl acetate to form crystals. The resulting crude crystals were subjected to recrystallization from DMF to give 1-(3-nitrophenyl)-3-(pyridin-2-ylmethyl)-1,8-naphthyridin-2 (1H)-one, mp 229 to 231° C./DMF (yield 67%).

¹H NMR(CDCl₃) δ: 4.17(2H, s), 7.15–7.21(2H, m), 7.41–7.45(1H, app-d, J=7.92 Hz), 7.61–7.77(4H, m), 7.89–7.93(1H, app-dd, J=1.98 Hz, 7.59 Hz), 8.17–8.19(1H, app-t, J=1.98 Hz), 8.32–8.37 (2H, m), 8.55–8.58(1H, m).

Example 2

1-(3-Nitrophenyl)-3-(pyridin-3-ylmethyl)-1,8-naphthyridin-2(1H)-one

The procedure of Example 1 was repeated using 2-(3-nitrophenylamino)nicotinaldehyde (1.0 eq.), ethyl 3-(pyridin-3-yl)propionate (1.2 eq., prepared in Synthetic Example 5) and LDA (1.5 eq.) to obtain 1-(3-nitrophenyl)-3-(pyridin-3-ylmethyl)-1,8-naphthyridin-2(1H)-one, mp 226 to 227° C./DMF.

¹H NMR(CDCl₃) δ: 4.10(2H, s), 7.18–7.22(1H, app-dd, J=4.62 Hz, 7.59 Hz), 7.27–7.31(1H, m), 7.50 (1H, s), 7.62–7.78(3H, m), 7.86–7.89(1H, app-dd, J=1.65, 7.59 Hz), 8.19–8.20(1H, app-t, J=1.98 Hz), 8.35–8.39(2H, m), 8.53–8.55(1H, app-dd, J=1.65 Hz, 4.62 Hz), 8.61–8.62(1H, app-d, J=1.98 Hz).

Example 3

1-(3-Cyanophenyl)-3-(pyridin-4-ylmethyl)-1,8-naphthyridin-2(1H)-one

The procedure of Example 1 was repeated using 2-(3-cyanophenylamino)nicotinaldehyde (1.0 eq., prepared according to the procedure of Example 3 in JP, A, 62-228076 (1987)), ethyl 3-(pyridin-4-yl)propionate (1.1 eq., prepared in Synthetic Example 6) and LDA (1.5 eq.) to obtain 1-(3-cyanophenyl)-3-(pyridin-4-ylmethyl)-1,8-naphthyridin-2(1H)-one, mp 229 to 230° C./DMF.

¹H NMR (CDCl₃) δ: 3.99 (2H, s), 7.18–7.29 (2H, m), 7.50 (1H, s), 7.51–7.90 (5H, m), 8.38–8.41 (1H, m), 8.56–8.59 (2H, m).

Example 4

1-(3-Nitrophenyl)-3-(pyridin-4-ylmethyl)-1,8-naphthyridin-2(1H)-one

The procedure of Example 1 was repeated using 2-(3-nitrophenylamino)nicotinaldehyde (1.0 eq.), ethyl 3-(pyridin-4-yl)propionate (1.1 eq.) and LDA (1.5 eq.) to obtain a product which was subjected to recrystallization from ethyl acetate-methanol to give 1-(3-nitrophenyl)-3-(pyridin-4-ylmethyl)-1,8-naphthyridin-2(1H)-one as a pale brown powder, mp 230° C./EtOAc-MeOH (decomp.).

¹H NMR (CDCl₃) δ: 4.00 (2H, s), 7.19–7.29 (3H, m), 7.52 (1H, s), 7.63–7.91 (4H, m), 8.19–8.59 (4H, m).

Example 5

1-(3-Nitrophenyl)-3-[2-(pyridin-3-yl)ethyl]-1,8-naphthyridin-2(1H)-one

The procedure of Example 1 was repeated using 2-(3-nitrophenylamino)nicotinaldehyde (1.0 eq.), methyl 4-(pyridin-3-yl)butanoate (1.3 eq., prepared in Synthetic Example 7) and LDA (1.3 eq.) to obtain 1-(3-nitrophenyl)-3-[2-(pyridin-3-yl)ethyl]-1,8-naphthyridin-2(1H)-one, mp 221 to 223° C./DMF, wherein the product was purified through silica gel column chromatography and recrystallization.

¹H NMR(CDCl₃) δ: 2.96–3.08(4H, m), 7.18–7.22(1H, app-dd, J=4.9 Hz, 5.6 Hz), 7.22–7.27(1H, app-dd, J=4.6 Hz, 7.6 Hz), 7.55 (1H, s), 7.56–7.61(1H, app-dt, J=2.3 Hz, 7.6 Hz), 7.64–7.68 (1H,m), 7.74–7.80(1H, app-t, J=7.9 Hz), 7.86–7.89(1H, app-dd, J=1.6 Hz, 7.6 Hz), 8.20–8.21(1H, app-t, J=2.3 Hz), 8.36–8.40 (2H, m), 8.46–8.50(2H, m).

Example 6

1-(3-Nitrophenyl)-3-[2-(pyridin-4-yl)ethyl]-1,8-naphthyridin-2(1H)-one

The procedure of Example 1 was repeated using 2-(3-nitrophenylamino)nicotinaldehyde (1.0 eq.), methyl 4-(pyridin-4-yl)butanoate (1.1 eq., prepared in Synthetic Example 8) and LDA (1.5 eq.) to obtain 1-(3-nitrophenyl)-3-[2-(pyridin-4-yl)ethyl]-1,8-naphthyridin-2(1H)-one, mp 213 to 214° C./DMF-EtOH.

¹H NMR(CDCl₃) δ: 3.01(4H, s), 7.17–7.23 (3H, m), 7.55(1H, s), 7.65–7.89(3H, m), 8.21–8.22 (1H, m), 8.36–8.39(2H, m), 8.51(2H, d, J=5.3 Hz).

Example 7

1-(3-Nitrophenyl)-3-[3-(pyridin-3-yl)propyl]-1,8-naphthyridin-2(1H)-one

The procedure of Example 1 was repeated using 2-(3-nitrophenylamino)nicotinaldehyde (1.0 eq.), ethyl 5-(pyridin-3-yl)pentanoate (1.1 eq., prepared in Synthetic Example 9) and LDA (1.5 eq.) to obtain 1-(3-nitrophenyl)-3-[3-(pyridin-3-yl)propyl]-1,8-naphthyridin-2(1H)-one, mp 172 to 173° C./DMF-EtOH. ¹H NMR(CDCl₃) δ: 2.02–2.11 (2H, m), 2.71–2.79 (4H, m), 7.18–7.24 (2H, m), 7.54–7.92 (5H, m), 8.19–8.20 (1H, m), 8.34–8.49(4H, m).

Example 8

1-(3-Nitrophenyl)-3-[3-(pyridin-4-yl)propyl]-1,8-naphthyridin-2(1H)-one

The procedure of Example 1 was repeated using 2-(3-nitrophenylamino)nicotinaldehyde (1.0 eq.), ethyl 5-(pyridin-4-yl)pentanoate (1.5 eq., prepared in Synthetic Example 10) and LDA (1.5 eq.) to obtain 1-(3-nitrophenyl)-3-[3-(pyridin-4-yl)propyl]-1,8-naphthyridin-2(1H)-one, mp 209 to 210° C./DMF-EtOH.

¹H NMR(CDCl₃) δ: 2.00–2.12(2H, m), 2.70–2.79(4H, m), 7.15–7.23 (3H, m), 7.61–7.67(2H, m), 7.75(1H, t, J=7.9 Hz), 7.89–7.93(1H, m), 8.19–8.20(2H, m), 8.34–8.38(2H, m), 8.50(2H, d, J=5.9 Hz).

Example 9

1-(3-Chlorophenyl)-3-[3-(pyridin-4-yl)propyl]-1,8-naphthyridin-2(1H)-one

The procedure of Example 1 was repeated using 2 (3 chlorophenylamino)nicotinaldehyde (1.0 eq., prepared according to the procedure of Example 3 in JP, A, 62-228076 (1987)), ethyl 5-(pyridin-4-yl)pentanoate (1.5 eq.) and LDA (1.5 eq.) to obtain 1-(3-chlorophenyl)-3-[3-(pyridin-4-yl)propyl]-1,8-naphthyridin-2(1H)-one, mp 148 to 149° C./AcOEt.

¹H NMR(CDCl₃) δ: 2.05(2H, quart, J=7.7 Hz), 2.73(4H, q, J=7.4 Hz), 7.14–7.20(4H, m), 7.28–7.30(1H, m), 7.44–7.51(2H, m), 7.60(1H, s), 7.86(1H, app-dd, J=2.0, 8.0 Hz), 8.41(1H, q, J=2.0 Hz), 8.49 (2H, app-dd, J=1.6, 4.3 Hz).

Example 10

1-(3-Methylthiophenyl)-3-[3-(pyridin-4-yl)propyl]-1,8-naphthyridin-2(1H)-one

The procedure of Example 1 was repeated using 2-(3-methylthiophenylamino)nicotinaldehyde (1.0 eq., prepared according to the procedure of Example 3 in JP, A, 62-228076 (1987)), ethyl 5-(pyridin-4-yl)pentanoate (2.0 eq.) and LDA (2.0 eq.) to obtain 1-(3-methylthiophenyl)-3-[3-(pyridin-4-yl)propyl]-1,8-naphthyridin-2(1H)-one, mp 137 to 138° C./DMF, wherein the product was purified through silica gel column chromatography and recrystallization.

$^1$H NMR(CDCl$_3$) δ: 2.00–2.11(2H, m), 2.49(3H, s), 2.70–2.77(4H, m), 7.02–7.06(1H, m), 7.11–7.17(4H, m), 7.34–7.38(1H, app-dt, J=1.3 Hz, 8.6 Hz), 7.45–7.51(1H, app-t, J=7.9 Hz), 7.56(1H, s), 7.84–7.87(1H, app-dd, J=2.0 Hz, 7.9 Hz) 8.41–8.43(1H, app-dd, J=1.7 Hz, 4.6 Hz), 8.48–8.50(2H, app-d, J=5.9 Hz).

Example 11

7-Methyl-1-(3-nitrophenyl)-3-[3-(pyridin-4-yl)propyl]-1,8-naphthyridin-2(1H)-one The procedure of Example 1 was repeated using 6-methyl-2-(3-nitrophenylamino)nicotinaldehyde (1.0 eq., prepared in Synthetic Example 1), ethyl 5-(pyridin-4-yl)pentanoate (1.5 eq.) and LDA (1.5 eq.) to obtain 7-methyl-1-(3-nitrophenyl)-3-[3-(pyridin-4-yl)propyl]-1,8-naphthyridin-2(1H)-one, mp 165 to 166° C./AcOEt, wherein the product was purified through silica gel column chromatography and recrystallization.

$^1$H NMR(CDCl$_3$) δ: 1.99–2.10(2H, m), 2.39(3H, s), 2.68–2.77(4H, m), 7.03–7.06(1H, app-d, J=7.9 Hz), 7.17–7.16(2H, app-d, J=5.9 Hz), 7.56(1H, s), 7.61–7.77(3H, m), 8.17–8.19(1H, app-t, J=1.7 Hz), 8.32–8.36(1H, m), 8.48–8.50(2H, app-d, J=5.9 Hz).

Example 12

7-Methyl-1-(3-methylthiophenyl)-3-[3-(pyridin-4-yl)propyl]-1,8-naphthyridin-2(1H)-one The procedure of Example 1 was repeated using 6-methyl-2-(3-methylthiophenylamino)nicotinaldehyde (1.0 eq., prepared in Synthetic Example 2), ethyl 5-(pyridin-4-yl)pentanoate (1.5 eq.) and LDA (1.5 eq.) to obtain 7-methyl-1-(3-methylthiophenyl)-3-[3-(pyridin-4-yl)propyl]-1,8-naphthyridin-2(1H)-one, mp 158 to 159° C./AcOEt, wherein the product was purified through silica gel column chromatography and recrystallization.

$^1$H NMR(CDCl$_3$) δ: 1.98–2.10(2H, m), 2.41(3H, s), 2.49 (3H, s), 2.67–2.76(4H, m), 6.99–7.04(2H, m), 7.11–7.16 (3H, m), 7.32–7.36 (1H, m), 7.42–7.48(1H, m), 7.52(1H, s), 7.70–7.73(1H, app-d, J=7.9 Hz), 8.48–8.50(2H, app-d, J=6.0 Hz).

Example 13

1-(3-Nitrophenyl)-3-[4-(pyridin-2-yl)butyl]-1,8-naphthyridin-2(1H)-one

The procedure of Example 1 was repeated using 2-(3-nitrophenylamino)nicotinaldehyde (1.0 eq.), ethyl 6-(pyridin-2-yl)hexanoate (2.0 eq., prepared in Synthetic Example 11) and LDA (2.0 eq.) to obtain 1-(3-nitrophenyl)-3-[4-(pyridin-2-yl)butyl]-1,8-naphthyridin-2(1H)-one, mp 163 to 165° C./DMF, wherein the product was purified through silica gel column chromatography and recrystallization.

$^1$H NMR(CDCl$_3$) δ: 1.72–1.94(4H, m), 2.73(2H, t, J=7.6 Hz), 2.86 (2H, t, J=6.9 Hz), 7.08–7.21(3H, m), 7.60(1H, s), 7.56–7.67(2H, m), 7.71–7.77(1H, app-t, J=9.3 Hz), 7.87–7.91(1H, app-dd, J=1.3 Hz, 7.61 Hz), 8.18–8.20(1H, m), 8.33–8.37(2H, m), 8.51–8.53 (1H, app-d, J=4.6 Hz).

Example 14

1-(3-Nitrophenyl)-3-[4-(pyridin-3-yl)butyl]-1,8-naphthyridin-2(1H)-one

The procedure of Example 1 was repeated using 2-(3-nitrophenylamino)nicotinaldehyde (1.0 eq.), methyl 6-(pyridin-3-yl)hexanoate (2.0 eq., prepared in Synthetic Example 12) and LDA (2.0 eq.) to obtain 1-(3-nitrophenyl)-3-[4-(pyridin-3-yl)butyl]-1,8-naphthyridin-2(1H)-one, mp 184.4 to 185.2° C./DMF, wherein the product was purified through silica gel column chromatography and recrystallization.

$^1$H NMR(CDCl$_3$) δ: 1.67–1.83(4H, m), 2.67–2.74(4H, m), 7.17–7.23(2H, m), 7.49–7.53(1H, app-dt, J=1.7 Hz, 7.9 Hz), 7.58(1H, s), 7.63–7.67(1H, app-dt, J=1.7 Hz, 7.9 Hz), 7.72–7.78(1H, app-t, J=7.9 Hz), 7.88–7.91(1H, app-dd, J=1.7 Hz, 7.6 Hz), 8.19–8.21(1H, app-t, J=2.0 Hz), 8.34–8.38(2H, m), 8.43–8.47(2H, m).

Example 15

1-(3-Nitrophenyl)-3-[4-(pyridin-4-yl)butyl]-1,8-naphthyridin-2(1H)-one

The procedure of Example 1 was repeated using 2-(3-nitrophenylamino)nicotinaldehyde (1.0 eq.), methyl 6-(pyridin-4-yl)hexanoate (2.0 eq., prepared in Synthetic Example 13) and LDA (2.0 eq.) to obtain 1-(3-nitrophenyl)-3-[4-(pyridin-4-yl)butyl]-1,8-naphthyridin-2(1H)-one, mp 168.8 to 169.6° C./DMF, wherein the product was purified through silica gel column chromatography and recrystallization.

$^1$H NMR(CDCl$_3$) δ: 1.74–1.77(4H, m), 2.66–2.74(4H, m), 7.11–7.13 (2H, app-d, J=5.6 Hz), 7.17–7.22(1H, app-dd, J=5.0 Hz, 7.9 Hz), 7.57(1H, s), 7.63–7.67(1H, m), 7.72–7.78 (1H, app-t, J=7.9 Hz), 7.88–7.91(1H, app-dd, J=1.7 Hz, 7.6 Hz), 8.19–8.20(1H, app-t, J=1.7 Hz), 8.34–8.38(2H, m), 8.48–8.50(2H, m).

Example 16

1-(3-Nitrophenyl)-3-[5-(pyridin-3-yl)pentyl]-1,8-naphthyridin-2(1H)-one

The procedure of Example 1 was repeated using 2-(3-nitrophenylamino)nicotinaldehyde (1.0 eq.), methyl 7-(pyridin-3-yl)heptanoate (2.0 eq., prepared in Synthetic Example 14) and LDA (2.0 eq.) to obtain 1-(3-nitrophenyl)-3-[5-(3-pyridyl)pentyl]-1,8-naphthyridin-2(1H)-one, mp 155° C./DMF, wherein the product was purified through silica gel column chromatography and recrystallization.

$^1$H NMR(CDCl$_3$) δ: 1.41–1.53(2H, m), 1.65–1.79(4H, m), 2.61–2.70 (4H, m), 7.17–7.22(2H, app-dd, J=4.6 Hz, 7.6 Hz), 7.47–7.51(1H, app-dt, J=1.7 Hz, 7.6 Hz), 7.59(1H, s), 7.63–7.67(1H, m), 7.71–7.77(1H, app-t, J=7.9 Hz), 7.89–7.92(1H, app-dd, J=1.7 Hz, 7.6 Hz), 8.19–8.20(1H, app-t, J=2.0 Hz), 8.34–8.45(4H, m).

Example 17

1-(3-Nitrophenyl)-3-[5-(pyridin-4-yl)pentyl]-1,8-naphthyridin-2(1H)-one

The procedure of Example 1 was repeated using 2-(3-nitrophenylamino)nicotinaldehyde (1.0 eq.), methyl 7-(pyridin-4-yl)heptanoate (2.0 eq., prepared in Synthetic Example 15) and LDA (2.0 eq.) to obtain 1-(3-nitrophenyl)-3-[5-(pyridin-4-yl)pentyl]-1,8-naphthyridin-2(1H)-one, mp 188.8 to 189.6° C./DMF, wherein the product was purified through silica gel column chromatography and recrystallization.

$^1$H NMR(CDCl$_1$) δ: 1.44–1.52(2H, m), 1.60–1.75(4H, m), 2.60–2.70 (4H, m), 7.10–7.12(2H, app-d, J=5.9 Hz), 7.18–7.22(1H, app-dd, J=4.6 Hz, 7.6 Hz), 7.58(1H, s), 7.63–7.67(1H, m), 7.72–7.78(1H, app-t, J=8.3 Hz), 7.88–7.92(1H, app-dd, J=2.0 Hz, 7.9 Hz), 8.19–8.20(1H, app-t, J=2.3 Hz), 8.34–8.38(2H, m), 8.47–8.49(2H, app-d, J=5.6 Hz).

Example 18

1-(3-Nitrophenyl)-3-[7-(pyridin-4-yl)heptyl]-1,8-naphthyridin-2(1H)-one

The procedure of Example 1 was repeated using 2-(3-nitrophenylamino)nicotinaldehyde (1.0 eq.), methyl 9-(pyridin-4-yl)nonanoate (1.5 eq., prepared in Synthetic Example 16) and LDA (1.5 eq.) to obtain 1-(3-nitrophenyl)-3-[7-(pyridin-4-yl)heptyl]-1,8-naphthyridin-2(1H)-one, mp 189 to 192° C./DMF, wherein the product was purified through silica gel column chromatography and recrystallization.

$^1$H NMR(CDCl$_3$) δ: 1.33–1.73(10H, m), 2.57–2.69(4H, m), 7.09–7.11 (2H, app-d, J=5.9 Hz),7.17–7.22(1H, app-dd, J=4.9 Hz, 7.6 Hz), 7.59(1H, s), 7.63–7.67(1H, m), 7.71–7.77 (1H, app-t, J=7.9 Hz), 7.89–7.92(1H, app-dd, J=1.6 Hz, 7.6 Hz), 8.19–8.21(1H, app-t, J=2.0 Hz), 8.34–8.38(2H, m), 8.46–8.48(2H, app-dd, J=1.3 Hz, 4.3 Hz).

Example 19

1-(3-Nitrophenyl)-3-[2-(2-thienyl)ethyl]-1,8-naphthyridin-2(1H)-one

The procedure of Example 1 was repeated using 2-(3-nitrophenylamino)nicotinaldehyde (1.0 eq.), ethyl 4-(2-thienyl)butanoate (1.5 eq., prepared in Synthetic Example 17) and LDA (1.5 eq.) to obtain 1-(3-nitrophenyl)-3-[2-(2-thienyl)ethyl]-1,8-naphthyridin-2(1H)-one, mp 175 to 176° C./DMF, wherein the product was purified through silica gel column chromatography and recrystallization.

$^1$H NMR(CDCl$_3$) δ: 3.05(2H, t, J=7.6 Hz), 3.26(2H, t, J=7.6 Hz), 6.82–6.84(1H, m), 6.90–6.93(1H, app-dd, J=3.3 Hz, 4.9 Hz), 7.12–7.14(1H, app-dd, J=1.3 Hz, 5.3 Hz), 7.17–7.21(1H, app-dd, J=4.9 Hz, 7.6 Hz), 7.56(1H, s), 7.64–7.68(1H, m), 7.73–7.79(1H, app-t, J=7.9 Hz), 7.85–7.89(1H, app-dd, J=1.7 Hz, 7.6 Hz), 8.20–8.22(1H, app-t, J=1.7 Hz), 8.35–8.39(2H, m).

Example 20

1-(3-Nitrophenyl)-3-[3-(2-furyl)propyl]-1,8-naphthyridin-2(1H)-one

The procedure of Example 1 was repeated using 2-(3-nitrophenylamino)nicotinaldehyde (1.0 eq.), ethyl 5-(2-furyl)pentanoate (1.5 eq., prepared in Synthetic Example 18) and LDA (1.5 eq.) to obtain 1-(3-nitrophenyl)-3-[3-(2-furyl) propyl]-1,8-naphthyridin-2(1H)-one, mp 166 to 167° C./DMF, wherein the product was purified through silica gel column chromatography and recrystallization.

$^1$H NMR(CDCl$_3$) δ: 2.01–2.12(2H, m), 2.71–79(4H, m), 6.04–6.06 (1H, app-dd, J=0.7 Hz, 3.3 Hz), 6.28-6.29(1H, app-dd, J=1.7 Hz, 3.3 Hz), 7.17–7.22(1H, app-dd, J=4.6 Hz, 7.6 Hz), 7.30–7.31(1H, app-dd, J=0.7 Hz, 1.7 Hz), 7.62(1H, s), 7.63–7.67(1H, m), 7.72–7.78(1H, app-t, J=7.9 Hz), 7.89–7.92(1H, app-dd, J=1.6 Hz, 7.6 Hz), 8.19–8.21(1H, app-t, J=2.0 Hz), 8.34–8.38(2H, m).

Example 21

1-(3-Nitrophenyl)-3-[3-(3-furyl)propyl]-1,8-naphthyridin-2(1H)-one

The procedure of Example 1 was repeated using 2-(3-nitrophenylamino)nicotinaldehyde (1.0 eq.), ethyl 5-(3-furyl)pentanoate (1.5 eq., prepared in Synthetic Example 19) and LDA (1.5 eq.) to obtain 1-(3-nitrophenyl)-3-[3-(3-furyl) propyl]-1,8-naphthyridin-2(1H)-one, mp 185 to 186° C./DMF, wherein the product was purified through silica gel column chromatography and recrystallization.

$^1$H NMR(CDCl$_3$) δ; 1.91–2.03(2H, m), 2.56(2H, t, J=7.6 Hz), 2.73(2H, t, J=7.6 Hz), 6.31–6.32(1H, m), 7.18–7.22 (1H, m), 7.25–7.27 (1H, m), 7.35–7.36(1H, app-t, J=1.7 Hz), 7.61(1H, s), 7.63–7.68 (1H, m), 7.12–7.78(1H, app-t, J=7.9 Hz), 7.89–7.92(1H, app-dd, J=2.0 Hz, 7.9 Hz), 8.19–8.21 (1H, m), 8.34–8.38(2H, m).

Example 22

1-(3-Nitrophenyl)-3-[4-(benzothiazol-2-yl)butyl]-1,8-naphthyridin-2(1H)-one

The procedure of Example 1 was repeated using 2-(3-nitrophenylamino)nicotinaldehyde (1.0 eq.), ethyl 6-(benzothiazol-2-yl)hexanoate (1.5 eq., prepared according to the procedure of Example 13 in JP, A, 8-208631 (1996)) and LDA (1.5 eq.) to obtain 1-(3-nitrophenyl)-3-[4-(benzothiazol-2-yl)butyl]-1,8-naphthyridin-2(1H)-one, mp 167.5 to 169.5° C./DMF, wherein the product was purified through silica gel column chromatography and recrystallization.

$^1$H NMR(CDCl$_3$) δ: 1.80–1.91(2H, m), 1.98–2.09(2H, m), 2.76(2H, J=7.9 Hz), 3.20(2H, J=7.6 Hz), 7.16–7.21(1H, app-dd, J=4.6 Hz, 7.6 Hz), 7.32–7.39(1H, m), 7.43–7.49(1H, m), 7.61(1H, s), 7.62–7.66(1H, m), 7.70–7.71(1H, app-t, J=7.9 Hz), 7.83–7.90(2H, m), 7.95–7.99(1H, m), 8.19–8.21 (1H,app-t, J=2.0 Hz), 8.34–8.38(2H, m).

Example 23

1-(Pyridin-3-yl)-3-[3-(pyridin-4-yl)propyl]-1,8-naphthyridin-2(1H)-one

The procedure of Example 1 was repeated using 2-(pyridin-3-ylamino)nicotinaldehyde (1.0 eq., prepared in Synthetic Example 3), ethyl 5-(pyridin-4-yl)pentanoate (1.5 eq., prepared in Synthetic Example 10) and LDA (1.5 eq.) to obtain 1-(pyridin-3-yl)-3-[3-(pyridin-4-yl)propyl]-1,8-naphthyridin-2(1H)-one, mp 178 to 180° C./DMF-EtOH.

$^1$H NMR(CDCl$_3$) δ: 2.00–2.11(2H, m), 2.70–2.78(4H, m), 7.15–7.21 (3H, m), 7.49–7.54(1H, m), 7.59(1H, s), 7.65–7.69(1H, m), 7.86–7.90(1H, app-dd, J=1.7 Hz, 7.7 Hz), 8.36–8.39(1H, app-dd, J=1.7 Hz, 4.7 Hz), 8.49–8.51(2H, app-d, J=5.8 Hz), 8.54–8.55(1H, m), 8.70–8.72(1H, app-dd, J=1.7 Hz, 4.9 Hz).

Example 24

1-(3-Nitrophenyl)-3-[3-(1-oxypyridin-4-yl)propyl]-1,8-naphthyridin-2(1H)-one

To a solution of 1-(3-nitrophenyl)-3-[3-(pyridin-4-yl) propyl]-1,8-naphthyridin-2(1H)-one (200 mg, 0.52 mmol, obtained in Example 8) in CHCl$_3$ (20 ml) was added dropwise a solution of m-chloroperbenzoic acid (purity 70%, 127.5 mg, 1.0 eq.) in CHCl$_3$ (4 ml) while ice cooling, and a solution of m-chloroperbenzoic acid (purity 70%, 25.5 mg, 0.2 eq.) in CHCl$_3$ (1 ml) was further added dropwise three times while monitoring the reaction by TLC. The organic layer was treated according to conventional techniques, evaporated, purified through silica gel column chromatography, and then recrystallized from DMF to give 1-(3-nitrophenyl)-3-[3-(1-oxypyridin-4-yl)propyl]-1,8-naphthyridin-2(1H)-one (134.1 mg), mp 247 to 249° C./DMF (yield 64%).

$^1$H NMR(CDCl$_3$) δ: 1.98–2.09(2H, m), 2.70–2.78(4H, m), 7.14–7.16(2H, app-d, J=6.9 Hz), 7.19–7.24(1H, app-dd, J=4.6 Hz, 7.6 Hz), 7.63(1H, s), 7.63–7.67(1H, m), 7.73–7.79 (1H, app-t, J=7.9 Hz), 7.90–7.93(1H, app-dd, J=1.7 Hz, 7.6 Hz), 8.12–8.15(2H, app-d, J=6.9 Hz), 8.19–8.20(1H, app-t, J=2.0 Hz), 8.35–8.39(2H, m).

Example 25

1-(3-Cyanophenyl)-3-[3-(pyridin-4-yl)propyl]-1,8-naphthyridin-2(1H)-one

The procedure of Example 1 was repeated using 2-(3-cyanophenylamino)nicotinaldehyde (1.0 eq.), ethyl 5-(4-pyridyl)pentanoate (1.2 eq., prepared in Synthetic Example 10) and LDA (1.2 eq.) to obtain 1-(3-cyanophenyl)-3-[3-(pyridin-4-yl)propyl]-1,8-naphthyridin-2(1H)-one, mp 202 to 203.5° C./DMF.

$^1$H NMR(CDCl$_3$) δ: 2.02–2.13(2H, m), 2.70–2.76(2H, t, J=7.9 Hz), 2.78–2.86(2H, t, J=7.9 Hz), 7.18–7.23(1H, app-dd, J=7.9 Hz, 4.9 Hz), 7.31–7.32(2H, app-d, J=5.9 Hz), 7.52–7.71(6H, m), 8.37–8.40(1H, app-dd, J=1.7 Hz, 4.9 Hz), 8.52–8.55(2H, app-d, J=5.9 Hz).

Example 26

1-(3-Methylsulfonylphenyl)-3-[3-(pyridin-4-yl)propyl]-1,8-naphthyridin-2(1H)-one The procedure of Example 1 was repeated using 2-(3-methyl-sulfonylphenylamino)nicotinaldehyde (1.0 eq., prepared in Synthetic Example 20), ethyl 5-(4-pyridyl) pentanoate (1.5 eq., prepared in Synthetic Example 10) and LDA (1.5 eq.) to obtain 1-(3-methylsulfonylphenyl)-3-[3-(pyridin-4-yl)propyl]-1,8-naphthyridin-2(1H)-one, mp 127 to 131° C./AcOEt, wherein the product was purified through flash column chromatography and recrystallization.

$^1$H NMR(CDCl$_3$) δ: 2.00–2.11(2H, m), 2.70–2.78(4H, m), 3.12 (3H, s), 7.15–7.17(2H, app-d, J=5.6 Hz), 7.17–7.21 (1H, app-dd, J=4.6 Hz, 7.6 Hz), 7.60(1H, s), 7.59–7.63(1H, m), 7.75–7.81(1H, app-t, J=7.9 Hz), 7.87–7.91(2H, m), 8.63–8.67(1H, m), 8.35–8.37 (1H, app-dd, J=1.7 Hz, 4.6 Hz), 8.49–8.51(2H, app-dd, J=1.7 Hz, 4.3 Hz).

Example 27

1-(3-Methylsulfonylphenyl)-3-[3-(1-oxypyridin-4-yl)propyl]-1,8-naphthyridin-2(1H)-one In the same manner as in Example 24, 1-(3-methylsulfonylphenyl)-3-[3-(pyridin-4-yl)propyl]-1,8-naphthyridin-2(1H)-one (1.0 eq., prepared in Example 26) was oxidized with m-chloroperbenzoic acid (3.4 eq.) to form 1-(3-methylsulfonylphenyl)-3-[3-(1-oxypyridin-4-yl) propyl]-1,8-naphthyridin-2(1H)-one, mp 184 to 187° C./DMF-AcOEt, wherein the product was purified through flash column chromatography and recrystallization.

$^1$H NMR(CDCl$_3$) δ: 1.98–2.09(2H, m), 2.70–2.78(4H, m), 3.13 (3H, s), 7.14–7.17(2H, app-d, J=6.6 Hz), 7.18–7.23 (1H, app-dd, J=4.9 Hz, 7.6 Hz), 7.60–7.64(1H, m), 7.62(1H, s), 7.76–7.82(1H, app-t, J=7.9 Hz), 7.89–7.92(1H, app-dd, J=1.7 Hz, 7.9 Hz), 8.04–8.07(1H, m), 8.13–8.15(2H, app-d, J=6.9 Hz), 8.36–8.38(1H, app-dd, J=1.6 Hz, 4.6 Hz).

Example 28

1-(3-Nitrophenyl)-3-[3-(pyridin-2-yl)propyl]-1,8-naphthyridin-2(1H)-one

The procedure of Example 1 was repeated using 2-(3-nitrophenylamino)nicotinaldehyde (1.0 eq.), ethyl 5-(2-pyridyl)pentanoate (1.5 eq., prepared in Synthetic Example 21) and LDA (1.5 eq.) to obtain 1-(3-nitrophenyl)-3-[3-(pyridin-2-yl)propyl]-1,8-naphthyridin-2(1H)-one, mp 201 to 202° C./DMF, wherein the product was purified through flash column chromatography and recrystallization.

$^1$H NMR(CDCl$_3$) δ: 2.11–2.23(2H, m), 2.76(2H, t, J=7.9 Hz), 2.94( 2H, t, J=7.9 Hz), 7.09–7.13(1H, m), 7.17–7.22 (2H, m), 7.57–7.67(2H, m), 7.66(1H, s), 7.717.77(1H, app-t, J=7.9 Hz), 7.88–7.92(1H, app-dd, J=2.0 Hz, 7.6 Hz), 8.19–8.20(1H, app-t, J=2.0 Hz), 8.34–8. 38(2H, m), 8.52–8.54(1H, m).

Example 29

1-(3-Nitrophenyl)-3-[2-(benzothiazol-2-yl)ethyl]-1,8-naphthyridin-2(1H)-one

The procedure of Example 1 was repeated using 2-(3-nitrophenylamino)nicotinaldehyde (1.0 eq.), methyl 4-(2-benzothiazolyl)butanoate (1.5 eq., prepared in Synthetic Example 22) and LDA (1.5 eq.) to obtain 1-(3-nitrophenyl)-3-[2-(benzothiazol-2-yl)ethyl]-1,8-naphthyridin-2(1H)-one, mp 178 to 179° C./DMF, wherein the product was purified through flash column chromatography and recrystallization.

$^1$H NMR(CDCl$_3$) δ: 3.29(2H, t, J=7.3 Hz), 3.57(2H, t, J=7.3 Hz), 7.16–7.21(1H, app-dd, 4.6 Hz, 7.6 Hz), 7.33–7.39(1H, m), 7.44–7.50(1H, m), 7.65–7.69(1H, m), 7.71(1H, s), 7.73–7.79 (1H, app-t, J=7.9 Hz), 7.83–7.86(1H, m), 7.86–7.90(1H, app-dd, J=1.7 Hz, 7.6 Hz), 7.97–8.01(1H, m), 8.21–8.22(1H, app-t, J=2.0 Hz), 8.36–8.40(2H, m).

Example 30

1-(3-Nitrophenyl)-3-[3-(benzothiazol-2-yl)propyl]-1,8-naphthyridin-2(1H)-one

The procedure of Example 1 was repeated using 2-(3-nitrophenylamino)nicotinaldehyde (1.0 eq.), methyl 5-(2-benzo-thiazolyl)pentanoate (1.5 eq., prepared in Synthetic Example 23) and LDA (1.5 eq.) to obtain 1-(3-nitrophenyl)-3-[3-(benzothiazol-2-yl)propyl]-1,8-naphthyridin-2(1H)-one, mp 185 to 186° C./DMF, wherein the product was purified through flash column chromatography and recrystallization.

$^1$H NMR(CDCl$_3$) δ: 2.32(2H, tt, 7.6 Hz, 7.6 Hz), 2.85(2H, t, J=7.6 Hz), 3.26(2H, t, J=7.6 Hz), 7.17–7.21(1H, app-dd, 4.6 Hz, 7.6 Hz), 7.32–7.38(1H, m), 7.42–7.48(1H, m), 7.62–7.66(1H, m), 7.67(1H, s), 7.72–7.78 (1H, app-t, J=7.9 Hz), 7.82–7.86(1H, m), 7.87–7.91(1H, app-dd, J=2.0 Hz, 7.9 Hz), 7.94–7.97(1H, m), 8.18–8.20(1H, app-t, J=2.0 Hz), 8.34–8.38(2H, m).

Example 31

1-(3-Nitrophenyl)-3-[3-(thiazol-2-yl)propyl]-1,8-naphthyridin-2(1H)-one

The procedure of Example 1 was repeated using 2-(3-nitrophenylamino)nicotinaldehyde (1.0 eq.), ethyl 5-(2- thiazolyl)pentanoate (1.5 eq., prepared in Synthetic Example 24) and LDA (1.5 eq.) to obtain 1-(3-nitrophenyl)-3-[3-(thiazol-2-yl)propyl]-1,8-naphthyridin-2(1H)-one, mp 198 to 199° C./DMF, wherein the product was purified through flash column chromatography and recrystallization.

$^1$H NMR(CDCl$_3$) δ: 2.45(2H, tt, J=7.6 Hz, 7.6 Hz), 2.81(2H, t, J=7.6 Hz), 3.18(2H, t, J=7.6 Hz), 7.18–7.23(1H, app-dd, J=4.6 Hz, 7.6 Hz), 7.22–7.23(1H, app-d, J=3.3 Hz), 7.63–7.68(1H, m), 7.68 (1H, s), 7.69–7.70(1H, app-d, J=3.3 Hz), 7.72–7.78(1H, app-t, J=7.9 Hz), 7.90–7.94(1H, app-dd, J=2.0 Hz, 7.9 Hz), 8.19–8.21(1H, app-t, J=2.0 Hz), 8.34–8.38(2H, m).

A variety of compounds covered by the general formula (1) as set forth in appended claims may be prepared by adoptations of the aforementioned procedures and synthetic routes and treatments as described in examples, or by adaptations of their modifications well known to those ordinarily skilled in the art, without necessitating extra experimentations.

Formulation Examples

Formulation Example 1

A formula for one tablet (total amount per tablet: 150 mg) is given below:

| | |
|---|---|
| Compound of the present invention | 20 mg |
| Crystalline Cellulose | 100 mg |
| Corn Starch | 28 mg |
| Magnesium Stearate | 2 mg |

The ingredients were formulated into tablets by known methods according to general pharmaceutical rules prescribed in JPXIII.

Formulation Example 2

A formula for one capsule (total amount per capsule: 180 mg) is given below:

| | |
|---|---|
| Compound of the present invention | 50 mg |
| Lactose | 100 mg |
| Corn Starch | 28 mg |
| Magnesium Stearate | 2 mg |

The ingredients were formulated into capsules by known methods according to general pharmaceutical rules prescribed in JPXIII.

Formulation Example 3

The compound of the present invention (10 mg) was dissolved in 3 ml of physiological saline. The solution was adjusted to pH 7 with 0.1 N aqueous sodium hydroxide, to which was added physiological saline to make the total volume 5 ml. The resulting solution was dispensed to each ampule, and then subjected to heat sterilization to obtain injections.

Formulation Example 4

To a mixture of the compound of the present invention (1 g), egg yolk lecithin (1.2 g), α-tocopherol (20 mg) and ascorbic acid (33 mg) was added purified water to make the total volume 100 ml. The resulting product was used as a pharmaceutical preparation for aerosols.

Formulation Example 5

The compound of the present invention (10 mg) was dissolved in a mixture of polyethylene glycol 300 (5.0 g), N-methyl-2-pyrrolidone (1.0 g) and Polysorbate 80 (1.0 g). The solution was passed through a 0.2 μm filter and dispensed to each ampule to obtain injections.

Formulation Example 6

A formula for ointments is given below:

| | |
|---|---|
| Compound of the present invention | 1.0 g |
| White Beeswax | 50 g |
| Sorbitan Sesquioleate | 20 g |
| Petrolatum | 30 g |

The ingredients were formulated into ointments by known methods according to general pharmaceutical rules prescribed in JPXIII.

Formulation Example 7

A formula for patches is given below:

| | |
|---|---|
| Compound of the present invention | 1.0 g |
| Boric Acid | 10 g |
| Concentrated Glycerin | 80 g |

The ingredients were blended to form a uniform mixture, spread in cloth, and shaped into patches (plasters).

Industrial Applicability

The present invention relates to novel 1,8-naphthyridin-2(1H)-one derivatives. The compounds of the present invention possess selective inhibition of PDE IV. For instance, the compounds selectively inhibit PDE IV predominantly present in bronchial smooth muscle cells and inflammatory cells, thereby leading to an elevation of cAMP levels in such cells, with the result that it may be expected to achieve relaxation of bronchial smooth muscle and suppression of inflammatory cell activation. The compounds are also less toxic as compared with the prior art PDE IV inhibitors. The present invention provides pharmaceutical compositions comprising an effective amount of the said 1,8-naphthyridin-2(1H)-one derivative, and also drugs for preventing or treating diseases associated with PDE IV activity. For example, the present invention enables the production of safer anti-asthmatics which possess excellent pharmacological properties.

While the present invention has been described specifically in detail with reference to certain embodiments and examples thereof, it would be apparent that it is possible to practice it in other forms. In light of the disclosure, it will be understood that various modifications and variations are within the spirit and scope of the appended claims.

What is claimed is:

1. A compound of the formula (1):

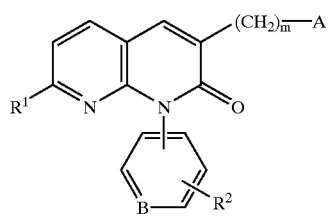

wherein:
- A is an unsubstituted or optionally substituted heteroaryl group selected from the group consisting of pyridyl, 1-oxopyridyl, thienyl, furyl, thiazolyl, benzothienyl, benzofuranyl, and benzothiazolyl,
- B is carbon,
- $R^1$ is hydrogen, lower alkyl, trifluoromethyl, hydroxyl, lower alkoxy, a noncyclic residue derived from a carboxylic acid or a derivative thereof, amino, or a noncyclic amino nitrogen-containing group,
- $R^2$ is hydrogen, halogen, cyano, nitro, lower alkylthio, lower alkylsulfinyl, lower alkylsulfonyl, trifluoromethyl, hydroxyl, lower alkoxy, a noncyclic residue derived from a carboxylic acid or a derivative thereof, amino, or a noncyclic amino nitrogen-containing group, and
- m is an integer of from 1 to 8, both inclusive; or a pharmaceutically acceptable salt thereof.

2. The compound according to claim 1, wherein A is pyridyl, 1-oxypyridyl, thienyl, furyl, or thiazolyl; or a pharmaceutically acceptable salt thereof.

3. The compound according to claim 1, wherein A is pyridyl or 1-oxypyridyl, and m is from 1 to 5, both inclusive; or a pharmaceutically acceptable salt thereof.

4. The compound according to claim 1, wherein A is benzothiazolyl; or a pharmaceutically acceptable salt thereof.

5. The compound according to claim 1, wherein $R^1$ is hydrogen or lower alkyl; or a pharmaceutically acceptable salt thereof.

6. The compound according to claim 1, wherein $R^2$ is hydrogen, halogen, cyano, nitro, lower alkylthio, lower alkylsulfinyl, or lower alkylsulfonyl; or a pharmaceutically acceptable salt thereof.

7. 1-(3-Nitrophenyl)-3-(pyridin-3-ylmethyl)-1,8-naphthyridin-2(1H)-one.

8. 1-(3-Nitrophenyl)-3-[3-(pyridin-4-yl)propyl]-1,8-naphthyridin-2(1H)-one.

9. 1-(3-Methylthiophenyl)-3-[3-(pyridin-4-yl)-propyl]-1,8-naphthyridin-2(1H)-one.

10. A pharmaceutical composition which comprises an effective amount of a compound according to any one of claims 1, 7, 8 or 9 a pharmaceutically acceptable salt thereof in admixture with a pharmaceutically acceptable carrier.

11. A method of treating bronchial asthma, said method comprising administering a therapeutically effective amount of a compound according to any one of claims 1, 9, 8 or 9 or a pharmaceutically acceptable salt thereof to a patient in need thereof.

12. The method of claim 1, wherein the bronchial asthma is chronic bronchial asthma or atopic asthma.

* * * * *

UNITED STATES PATENT AND TRADEMARK OFFICE
CERTIFICATE OF CORRECTION

PATENT NO.    : 6,642,250 B2
DATED         : November 4, 2003
INVENTOR(S)   : Tomoji Aotsuka et al.

It is certified that error appears in the above-identified patent and that said Letters Patent is hereby corrected as shown below:

Column 9,
Scheme (I), formula (1), please change the formula

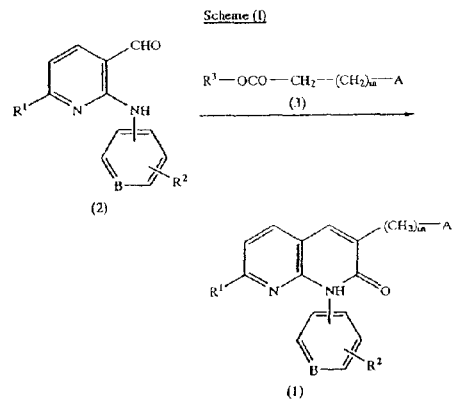

with the correct formula:

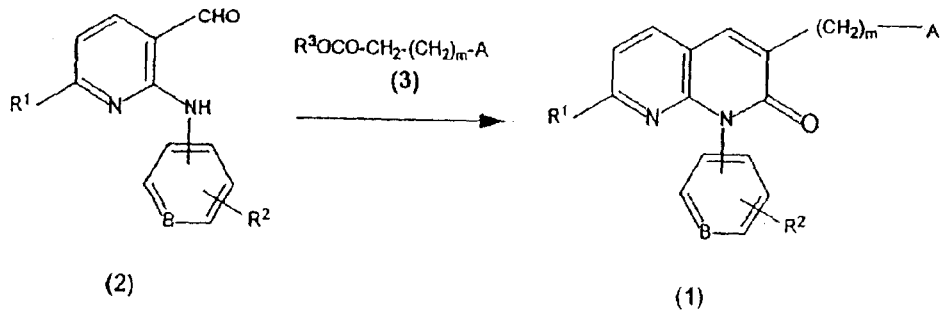

UNITED STATES PATENT AND TRADEMARK OFFICE
CERTIFICATE OF CORRECTION

PATENT NO. : 6,642,250 B2
DATED : November 4, 2003
INVENTOR(S) : Tomoji Aotsuka et al.

It is certified that error appears in the above-identified patent and that said Letters Patent is hereby corrected as shown below:

<u>Column 44,</u>
Line 24, after "9" please insert -- or --.
Line 28, please change the first "9" to -- 7 --.

Signed and Sealed this

Sixteenth Day of March, 2004

JON W. DUDAS
*Acting Director of the United States Patent and Trademark Office*